United States Patent
Nakano et al.

(10) Patent No.: US 12,305,104 B2
(45) Date of Patent: May 20, 2025

(54) AZO COMPOUND, COMPOSITION, FILM, LAMINATE, AND DISPLAY DEVICE

(71) Applicant: Sumitomo Chemical Company, Limited, Tokyo (JP)

(72) Inventors: Masaya Nakano, Osaka (JP); Masashi Asano, Tsukuba (JP); Eiji Yoshikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 18/039,667

(22) PCT Filed: Nov. 18, 2021

(86) PCT No.: PCT/JP2021/042412
§ 371 (c)(1),
(2) Date: May 31, 2023

(87) PCT Pub. No.: WO2022/118667
PCT Pub. Date: Jun. 9, 2022

(65) Prior Publication Data
US 2023/0416610 A1    Dec. 28, 2023

(30) Foreign Application Priority Data
Dec. 2, 2020  (JP) .................................. 2020-200221

(51) Int. Cl.
  *G02F 1/1333*  (2006.01)
  *C09B 46/00*  (2006.01)
  *C09K 19/60*  (2006.01)
  *G02B 5/30*  (2006.01)
  *H10K 59/80*  (2023.01)

(52) U.S. Cl.
  CPC ............ *C09K 19/601* (2013.01); *C09B 46/00* (2022.08); *G02B 5/3016* (2013.01); *H10K 59/8793* (2023.02)

(58) Field of Classification Search
  CPC .................................................... C09K 19/60
  See application file for complete search history.

(56) References Cited

U.S. PATENT DOCUMENTS

2017/0305930 A1   10/2017   Morimoto et al.
2017/0306237 A1   10/2017   Morimoto et al.

FOREIGN PATENT DOCUMENTS

| DE | 154020 A1 * | 2/1982 |
| JP | S6470585 A | 3/1989 |
| JP | H05323296 A | 12/1993 |
| JP | 2013227532 A | 11/2013 |
| JP | 2017090668 A | 5/2017 |
| JP | 2017197630 A | 11/2017 |
| JP | 2017198804 A | 11/2017 |
| WO | WO-2022153667 A1 * | 7/2022 |

OTHER PUBLICATIONS

"Photsensitive bent-core liquid crystals based on methyl substituted 3-hydroxybenzoic acid", Alaasar et al., RSC Adv., 2017,7, 35805-35813 (Year: 2017).*
Kohout et. al., "Photosensitive bent-core liquid crystals based on methyl substituted 3-hydroxybenzoic acid," RSC Advances, vol. 7, pp. 35805-35813 (2017).

* cited by examiner

*Primary Examiner* — Geraldina Visconti
(74) *Attorney, Agent, or Firm* — Panitch Schwarze Belisario & Nadel LLP

(57) ABSTRACT

An azo compound is represented by formula (1A). $L^1$ and $L^2$ each represent a divalent linking group or a single bond. y represents 1 or 2. p and q each represent 0 or 1, and at least one of p and q is 1. X represents an oxygen atom or $NR^5$, and $R^5$ represents a hydrogen atom or an aliphatic hydrocarbon group. $R^{12}$, $R^{13}$, and $R^{14}$ each represent an aliphatic hydrocarbon group, and may each have a polymerizable group. Q represents a single bond or a group selected from —OC(=O)—, —C(=O)O—, —C=C—, —CH=CH—, —N=N—, —NHC(=O)—, and —C(=O)NH—. $Ar^1$, $Ar^2$, and $Ar^3$ each represent a 1,4-phenylene group or a divalent sulfur-containing aromatic heterocyclic group. When y is 2, two $Ar^3$s may be the same or different.

(1A)

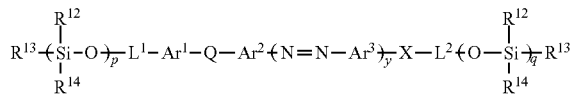

9 Claims, No Drawings

AZO COMPOUND, COMPOSITION, FILM, LAMINATE, AND DISPLAY DEVICE

CROSS-REFERENCE TO RELATED APPLICATIONS

This application is a Section 371 of International Application No. PCT/JP2021/042412, filed Nov. 18, 2021, which was published in the Japanese language on Jun. 9, 2022 under International Publication No. WO 2022/118667 A1, which claims priority under 35 U.S.C. § 119(b) to Japanese Application No. 2020-200221, filed Dec. 2, 2020, the disclosures of which are incorporated herein by reference in their entireties.

TECHNICAL FIELD

The present invention relates to an azo compound, a composition, a film, a laminate, and a display device.

BACKGROUND ART

As a polarizing film (optical film) used for a liquid crystal display device or the like, a polarizing film containing a dichroic dye is known. As the dichroic dye, an azo compound having a fused heterocyclic group is proposed in Patent Document 1. In addition, a dichroic dye compound having a fused heterocyclic group with improved solubility is proposed in Patent Document 2.

PRIOR ART DOCUMENTS

Patent Documents

Patent Document 1: JP-A-64-70585
Patent Document 2: WO-A-2017/090668

SUMMARY OF THE INVENTION

Problems to be Solved by the Invention

However, a composition for forming a polarizing film containing an azo compound described in Patent Document 1 has insufficient storage stability, and cannot obtain a high-quality polarizing film due to generation of defects in a formed film in some cases. Further improvement in solubility is also required for the dichroic dye compound described in Patent Document 2. An object of the present invention is to provide an azo compound capable of forming a high-quality film even when the azo compound is stored in a state of a composition containing a solvent for a predetermined time.

Means for Solving the Problems

The present invention provides the following [1] to [9].
[1] An azo compound represented by formula (1A).

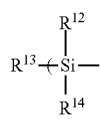

[In formula (1A), $L^1$ and $L^2$ each independently represent a divalent linking group or a single bond formed from at least one selected from the group consisting of a methylene group, an oxygen atom, and a carbonyl group.

y represents an integer of 1 or 2.

p and q each independently represent 0 or 1, and at least one of p and q is 1.

$R^{12}$, $R^{13}$, and $R^{14}$ each independently represent an aliphatic hydrocarbon group having 1 to 10 carbon atoms, an alkyloxy group having 1 to 10 carbon atoms, a trialkylsiloxy group having 3 to 10 carbon atoms, a trialkylsilyl group having 3 to 10 carbon atoms, or a phenyl group, these groups each optionally having a substituent, and a hydrogen atom of $R^{12}$, $R^{13}$, or $R^{14}$ may be replaced with a polymerizable group.

X represents an oxygen atom or $NR^5$.

$R^5$ represents a hydrogen atom or an aliphatic hydrocarbon group having 1 to 10 carbon atoms, and may be bonded to $R^{13}$ to form a ring.

Q represents a single bond or one group selected from the group consisting of —OC(=O)—, —C(=O)O—, —C≡C—, —CH=CH—, —N=N—, —NHC(=O)—, and —C(=O)NH—.

$Ar^1$, $Ar^2$, and $Ar^3$ each independently represent a 1,4-phenylene group optionally having a substituent or a divalent sulfur-containing aromatic heterocyclic group optionally having a substituent.

When y is 2, two $Ar^3$s may be the same or different.]

[2] The azo compound according to [1], represented by the following formula (1).

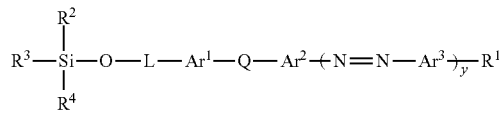

[In formula (1), L represents a divalent linking group or a single bond formed from at least one selected from the group consisting of a methylene group, an oxygen atom, and a carbonyl group.

y represents an integer of 1 or 2.

$R^1$ represents one group selected from the group consisting of a methylamino group, an ethylamino group, a dimethylamino group, a diethylamino group, an ethylmethylamino group, a pyrrolidyl group, an oxazolidinyl group, a piperidyl group, a morpholino group, a methoxy group, and an ethoxy group, and a hydrogen atom of each of these groups may be replaced with a polymerizable group.

$R^2$, $R^3$, and $R^4$ each independently represent an aliphatic hydrocarbon group having 1 to 10 carbon atoms, and a hydrogen atom of $R^2$, $R^3$, or $R^4$ may be replaced with a polymerizable group.

Q represents a single bond or one group selected from the group consisting of —OC(=O)—, —C(=O)O—, —C≡C—, —CH=CH—, —N=N—, —NHC(=O)—, and —C(=O)NH—.

$Ar^1$, $Ar^2$, and $Ar^3$ each independently represent a 1,4-phenylene group optionally having a substituent or a divalent sulfur-containing aromatic heterocyclic group optionally having a substituent.

When y is 2, two $Ar^3$s may be the same or different.]

[3] The azo compound according to [1] or [2], in which Q is —N=N— in the formula (1A) or (1).

[4] The azo compound according to any one of [1] to [3], in which at least one of $Ar^1$ and $Ar^2$ is a divalent sulfur-containing aromatic heterocyclic group in the formula (1A) or (1).

[5] A composition containing the azo compound according to any one of [1] to [4], and a liquid crystalline compound containing at least one of a polymerizable liquid crystal compound and a liquid crystalline polymer compound.

[6] The composition according to [5], in which the liquid crystalline compound is a smectic liquid crystalline compound.

[7] A film containing the composition according to [5] or [6] as a forming material.

[8] A laminate including the film according to [7].

[9] A display device including the film according to [7] or the laminate according to [8].

Effect of the Invention

The present invention can provide an azo compound capable of forming a high-quality film even when the azo compound is stored in a state of a composition containing a solvent for a predetermined time.

MODE FOR CARRYING OUT THE INVENTION

In the present specification, the term "step" includes not only an independent step but also a step that cannot be clearly distinguished from other steps as long as an intended purpose of the step is achieved. In addition, when a plurality of substances corresponding to each component is present in a composition, the content of each component in the composition means the total amount of the plurality of substances present in the composition unless otherwise specified. Furthermore, as an upper limit and a lower limit of a numerical range described in the present specification, numerical values exemplified as the numerical range can be arbitrarily selected and combined. Hereinafter, an embodiment of the present invention will be described in detail. Note that the scope of the present invention is not limited to the embodiment described here, and various modifications can be made without departing from the gist of the present invention.

Azo Compound

An azo compound according to the present embodiment is represented by the following formula (1A). The azo compound represented by the following formula (1A) (hereinafter, also referred to as azo compound (1A)) may be used, for example, as a dichroic dye as a material for forming a polarizing film. That is, the azo compound (1A) may be an active ingredient constituting the dichroic dye. The azo compound (1A) can form a high-quality film having excellent stability as a composition even when the azo compound (1A) is stored in a state of a composition containing a solvent for a predetermined time. The stability as a composition means that aggregation, precipitation, and the like of the azo compound (1A) in the composition are suppressed. In addition, the high-quality film may be, for example, a film in which precipitation of the azo compound (1A) is suppressed, or a polarizing film in which generation of orientation defects is suppressed. In addition, the storage for a predetermined time means, for example, storage at room temperature (25° C.) for one day or more, preferably five days or more.

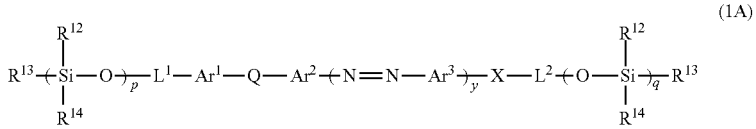

(1A)

In formula (1A), $L^1$ and $L^2$ each independently represent a divalent linking group or a single bond formed from at least one selected from the group consisting of a methylene group, an oxygen atom, and a carbonyl group. y represents an integer of 1 or 2. p and q each independently represent 0 or 1, and at least one of p and q is 1. $R^{12}$, $R^{13}$, and $R^{14}$ each independently represent an aliphatic hydrocarbon group having 1 to 10 carbon atoms, an alkyloxy group having 1 to 10 carbon atoms, a trialkylsiloxy group having 3 to 10 carbon atoms, a trialkylsilyl group having 3 to 10 carbon atoms, or a phenyl group, these groups each optionally having a substituent, and a hydrogen atom of $R^{12}$, $R^{13}$, or $R^{14}$ may be replaced with a polymerizable group. X represents an oxygen atom or $NR^5$. $R^5$ represents a hydrogen atom or an aliphatic hydrocarbon group having 1 to 10 carbon atoms, and may be bonded to $R^{13}$ to form a ring. Q represents a single bond or one group selected from the group consisting of —OC(=O)—, —C(=O)O—, —C≡C—, —CH=CH—, —N=N—, —NHC(=O)—, and —C(=O)NH—. $Ar^1$, $Ar^2$, and $Ar^3$ each independently represent a 1,4-phenylene group optionally having a substituent or a divalent sulfur-containing aromatic heterocyclic group optionally having a substituent. When y is 2, two $Ar^3$s may be the same or different.

Specific examples of the divalent linking group represented by $L^1$ or $L^2$ include an alkylene group having 1 to 4 carbon atoms, an alkyleneoxy group having 1 to 4 carbon atoms or an oxyalkylene group having 1 to 4 carbon atoms, an alkyleneoxycarbonyl group having 1 to 4 carbon atoms or a carbonyloxyalkylene group having 1 to 4 carbon atoms, an alkylenecarbonyloxy group having 1 to 4 carbon atoms or an oxycarbonylalkylene group having 1 to 4 carbon atoms, an alkylenecarbonyl group having 1 to 4 carbon atoms, and an alkylene group having 1 to 4 carbon atoms or a carbonylalkylene group having 1 to 4 carbon atoms. The number of atom groups (the number of atoms of a main chain) directly linking an oxygen atom to $Ar^1$ or X in formula (1A) may be 1 or more and 4 or less, and preferably 1 or more and 3 or less, or 2 or more and 3 or less from a viewpoint of stability as a composition containing the azo compound (1A). That is, the number of atoms constituting each of $L^1$ and $L^2$ excluding a hydrogen atom and a carbonyl oxygen may be 1 or more and 4 or less, and preferably 1 or more and 3 or less, or 2 or more and 3 or less.

$L_1$ and $L_2$ are preferably selected such that formula (1A) does not contain an oxygen-oxygen bond or an oxygen-nitrogen bond from a viewpoint of stability of the azo compound (1A). That is, when p=1, $L^1$ may be represented by the following formula (2), and when q=1, $L^2$ may be represented by the following formula (2a).

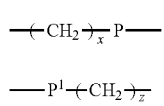

$$-\!\!\!+\!CH_2\!\!+\!\!\!\!-_x P-\!\!\!-\quad (2)$$

$$-\!\!\!-P^1\!\!-\!\!\!+\!CH_2\!\!+\!\!\!\!-_z\quad (2a)$$

In formula (2), x represents an integer of 0 to 4. P represents a single bond or one group selected from the group consisting of —O—, —OC(=O)—, and —C(=O)O—. Note that, when P is a single bond, —O—, or —OC(=O)—, x represents an integer of 1 to 4. P is preferably a single bond or —O—. When P is —C(=O)O—, x is an integer of 0 to 4, preferably 1, 2, or 3, and more preferably 2. When P is a single bond, —O—, or —OC(=O)—, x is preferably 2 or 3, and more preferably 2.

In formula (2a), z represents an integer of 0 to 4. $P^1$ represents a single bond, —C(=O)—, or —C(=O)O—. Note that, when $P^1$ is a single bond or —C(=O)O—, z represents an integer of 1 to 4. $P^1$ is preferably a single bond or —O—. When P is —C(=O)—, z is an integer of 0 to 4, preferably 1, 2, or 3, and more preferably 2. When $P^1$ is a single bond or —O—, z is preferably 2 or 3, and more preferably 2.

$R^{12}$, $R^{13}$, and $R^{14}$ each independently represent an aliphatic hydrocarbon group having 1 to 10 carbon atoms, an alkyloxy group having 1 to 10 carbon atoms, a trialkylsiloxy group having 3 to 10 carbon atoms, a trialkylsilyl group having 3 to 10 carbon atoms, or a phenyl group. $R^{12}$, $R^{13}$, and $R^{14}$ preferably each represent an aliphatic hydrocarbon group having 1 to 10 carbon atoms or a phenyl group, and more preferably each represent an aliphatic hydrocarbon group having 1 to 10 carbon atoms.

The aliphatic hydrocarbon group, the alkyloxy group, the trialkylsiloxy group, the trialkylsilyl group, or the phenyl group represented by $R^{12}$, $R^{13}$, or $R^{14}$ may each independently further have a substituent. Examples of the substituent in $R^{12}$, $R^{13}$, or $R^{14}$ include a polymerizable group, a halogen atom (a fluorine atom, a chlorine atom, or the like), a hydroxy group, an alkyl group having 1 to 6 carbon atoms, an alkoxy group having 1 to 6 carbon atoms, and a phenyl group. When $R^{12}$, $R^{13}$, or $R^{14}$ has a substituent, the total number of the substituents is, for example, 1 to 10, and preferably 1 to 6.

At least one hydrogen atom of the aliphatic hydrocarbon group, the alkyloxy group, the trialkylsiloxy group, the trialkylsilyl group, or the phenyl group represented by $R^{12}$, $R^{13}$, or $R^{14}$ may be replaced with a polymerizable group. Examples of the polymerizable group include a (meth)acrylate group ((meth)acryloyloxy group), a styryl group (vinylphenyl group), a vinyl group, and an epoxy group. The polymerizable group is preferably a radically polymerizable group, and is particularly preferably a (meth)acrylate group. When $R^{12}$, $R^{13}$, or $R^{14}$ has a polymerizable group as a substituent, the total number of the polymerizable groups is, for example, 1 or 2, and preferably 1.

The number of carbon atoms of the aliphatic hydrocarbon group represented by $R^{12}$, $R^{13}$, or $R^{14}$ is preferably 1 to 8, and more preferably 1 to 6. The aliphatic hydrocarbon group may be either branched or linear. Examples of the aliphatic hydrocarbon group include an alkyl group, an alkenyl group, and an alkynyl group, and an alkyl group is preferable. Specific examples of the alkyl group include a methyl group, an ethyl group, a propyl group, an isopropyl group, a butyl group, a tert-butyl group, a hexyl group, a 2,3-dimethyl-2-butyl group (1,1,2-trimethylpropyl group), and an octyl group. At least one of $R^{12}$, $R^{13}$, and $R^{14}$ is preferably a branched aliphatic hydrocarbon group, and more preferably a branched alkyl group. The number of carbon atoms of the branched aliphatic hydrocarbon group is, for example, 3 to 8, and preferably 3 to 6. The total number of carbon atoms contained in $R^{12}$, $R^{13}$, and $R^{14}$ in formula (1A) may be, for example, 3 or more and 24 or less, and is preferably 6 or more and 18 or less, and more preferably 6 or more and 16 or less.

The number of carbon atoms of the alkyloxy group represented by $R^{12}$, $R^{13}$, or $R^{14}$ is preferably 1 to 8, or 1 to 6. An alkyl group moiety of the alkyloxy group may be either branched or linear. At least one of $R^{12}$, $R^{13}$, and $R^{14}$ is preferably a branched alkyloxy group. The number of carbon atoms of the branched alkyloxy group is, for example, 3 to 8, and preferably 3 to 6. The total number of carbon atoms contained in $R^{12}$, $R^{13}$, and $R^{14}$ in formula (1A) may be, for example, 3 or more and 12 or less, and is preferably 6 or more and 12 or less, or 6 or more and 10 or less. Specific examples of the alkyloxy group include a methoxy group, an ethoxy group, a propyloxy group, an isopropyloxy group, a butoxy group, and a hexyloxy group.

The number of carbon atoms of an alkyl group moiety of the trialkylsiloxy group or trialkylsilyl group represented by $R^{12}$, $R^{13}$, or $R^{14}$ is 1 to 6, and preferably 1 to 5, or 1 to 4. The total number of carbon atoms of the alkyl group moiety of the trialkylsiloxy or trialkylsilyl group is preferably 3 to 8, or 3 to 6. Specific examples of the trialkylsiloxy group include a trimethylsilyloxy group, a triethylsilyloxy group, and a tert-butyldimethylsilyloxy group. Specific examples of the trialkylsilyl group include a trimethylsilyl group, a triethylsilyl group, and a tert-butyldimethylsilyl group.

X represents an oxygen atom or $NR^5$. $R^5$ represents a hydrogen atom or an aliphatic hydrocarbon group having 1 to 10 carbon atoms. The number of carbon atoms of the aliphatic hydrocarbon group represented by $R^5$ is preferably 1 to 8, or 1 to 6. The aliphatic hydrocarbon group may be either branched or linear. Examples of the aliphatic hydrocarbon group include an alkyl group, an alkenyl group, and an alkynyl group, and an alkyl group is preferable. Specific examples of the alkyl group include a methyl group, an ethyl group, and a propyl group. $R^5$ may be bonded to $R^{13}$ to form a ring. When $R^5$ and $R^{13}$ are bonded to each other to form a ring, q is preferably 0. The ring to be formed may be a nitrogen-containing aliphatic ring, and the number of members is, for example, 5 or 6. Examples of the ring formed by bonding $R^5$ and $R^{13}$ to each other include a pyrrolidyl group, a piperidyl group, an oxazolidinyl group, and a morpholyl group.

The azo compound represented by formula (1A) may preferably satisfy p=1 and q=0, and may be more preferably an azo compound represented by the following formula (1) (hereinafter, also referred to as azo compound (1)) from a viewpoint of further increasing a dichroic ratio.

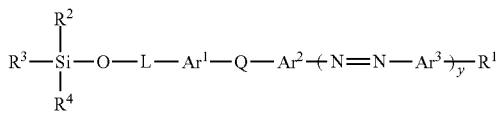
(1)

In formula (1), L represents a divalent linking group or a single bond formed from at least one selected from the group consisting of a methylene group (—$CH_2$—), an oxygen atom (—O—), and a carbonyl group (—C(=O)—). Specific examples of the divalent linking group represented by L include an alkylene group having 1 to 4 carbon atoms, an alkyleneoxy group having 1 to 4 carbon atoms, an alkyleneoxycarbonyl group having 1 to 4 carbon atoms, an alkylenecarbonyloxy group having 1 to 4 carbon atoms, and an alkylenecarbonyl group having 1 to 4 carbon atoms. The number of atom groups (the number of atoms of a main chain) directly linking an oxygen atom to $Ar^1$ in formula (1) may be 1 or more and 4 or less, and preferably 1 or more and 3 or less, or 2 or more and 3 or less from a viewpoint of stability of the azo compound (1) as a composition. That is, the number of atoms constituting L excluding a hydrogen atom and a carbonyl oxygen may be 1 or more and 4 or less, and preferably 1 or more and 3 or less, or 2 or more and 3 or less. The divalent linking group represented by L may be represented by, for example, the following formula (2), and the azo compound (1) may be represented by the following formula (1a).

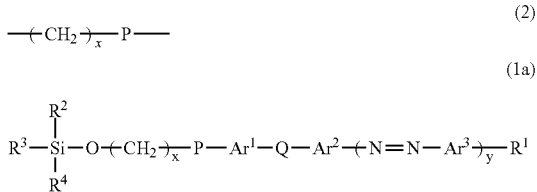

In formulas (2) and (1a), x represents an integer of 0 to 4. P represents a single bond or one group selected from the group consisting of —O—, —OC(=O)—, and —C(=O)O—. Note that, when P is a single bond, —O—, or —OC(=O)—, x represents an integer of 1 to 4. P is preferably a single bond or —O—. When P is —C(=O)O—, x is an integer of 0 to 4, preferably 1, 2, or 3, and more preferably 2. When P is a single bond, —O—, or —OC(=O)—, x is an integer of 1 to 4, preferably 2 or 3, and more preferably 2.

In formulas (1A), (1), and (1a), y represents an integer of 1 or 2. When y is 2, two $Ar^3$s may be the same or different.

In formulas (1) and (1a), $R^1$ represents one group selected from the group consisting of a methylamino group, an ethylamino group, a dimethylamino group, a diethylamino group, an ethylmethylamino group, a pyrrolidyl group, an oxazolyl group, an oxazolidinyl group, a piperidyl group, a morpholino group, a methoxy group, and an ethoxy group. $R^1$ is preferably a dimethylamino group, a diethylamino group, an ethylmethylamino group, a methoxy group, or an ethoxy group, and more preferably a dimethylamino group or a diethylamino group. At least one hydrogen atom of the group represented by $R^1$ may be replaced with a polymerizable group. Here, examples of the polymerizable group include a (meth)acrylate group ((meth)acryloyloxy group), a styryl group (vinylphenyl group), a vinyl group, and an epoxy group. The polymerizable group is preferably a radically polymerizable group, and is particularly preferably a (meth)acrylate group. When $R^1$ has a polymerizable group, the number of the polymerizable groups is, for example, 1 or 2, and preferably 1.

Q represents a single bond or one group selected from the group consisting of —OC(=O)—, —C(=O)O—, —C≡C—, —CH=CH—, —N=N—, —NHC(=O)—, and —C(=O)NH—. Q is preferably a single bond, —OC(=O)—, or —N=N—, and more preferably —N=N—.

$Ar^1$, $Ar^2$, and $Ar^3$ each independently represent a 1,4-phenylene group optionally having a substituent or a divalent sulfur-containing aromatic heterocyclic group optionally having a substituent. Examples of the sulfur-containing aromatic heterocyclic group include a thiazole diyl group, a benzothiazole diyl group, and a thienothiazole diyl group. A benzothiazole diyl group or a thienothiazole diyl group is preferable, a thienothiazole diyl group is more preferable, and a thieno [2,3-d] thiazole-2,5-diyl group is still more preferable. At least one of $Ar^1$ and $Ar^2$ is preferably a divalent sulfur-containing aromatic heterocyclic group optionally having a substituent, and more preferably a benzothiazole diyl group or a thienothiazole diyl group. Still more preferably, $Ar^2$ is a benzothiazole diyl group or a thienothiazole diyl group, and particularly preferably, $Ar^2$ is a thienothiazole diyl group. Examples of the substituent in $Ar^1$, $Ar^2$, and $Ar^3$ include a halogen atom, a hydroxy group, a methyl group, and a methoxy group. A fluorine atom, a chlorine atom, a hydroxy group, a methyl group, or a methoxy group is preferable, a fluorine atom, a chlorine atom, a hydroxy group, or a methyl group is more preferable, and a fluorine atom, a chlorine atom, or a methyl group is still more preferable. $Ar^1$, $Ar^2$, and $Ar^3$ each independently have 0, 1, or 2 substituents, preferably 0 or 1 substituent.

$R^2$, $R^3$, and $R^4$ each independently represent an aliphatic hydrocarbon group having 1 to 10 carbon atoms. The number of carbon atoms of the aliphatic hydrocarbon group represented by $R^2$, $R^3$, or $R^4$ is preferably 1 to 8, or 1 to 6. The aliphatic hydrocarbon group may be either branched or linear. Examples of the aliphatic hydrocarbon group include an alkyl group, an alkenyl group, and an alkynyl group, and an alkyl group is preferable. Specific examples of the alkyl group include a methyl group, an ethyl group, a propyl group, an isopropyl group, a butyl group, a tert-butyl group, a hexyl group, a 2,3-dimethyl-2-butyl group (1,1,2-trimethylpropyl group), and an octyl group. At least one of $R^2$, $R^3$, and $R^4$ is preferably a branched aliphatic hydrocarbon group, and more preferably a branched alkyl group. The number of carbon atoms of the branched aliphatic hydrocarbon group is, for example, 3 to 8, and preferably 3 to 6. The total number of carbon atoms contained in $R^2$, $R^3$, and $R^4$ in formula (1) or (1a) may be, for example, 3 or more and 24 or less, and is preferably 6 or more and 18 or less, and more preferably 6 or more and 16 or less. At least one hydrogen atom of the aliphatic hydrocarbon group represented by $R^2$, $R^3$, or $R^4$ may be replaced with a polymerizable group. When $R^2$, $R^3$, or $R^4$ has a polymerizable group, the total number of the polymerizable groups is, for example, 1 or 2, and preferably 1.

In an aspect, $R^2$, $R^3$, and $R^4$ may each independently represent an alkyloxy group having 1 to 10 carbon atoms, a trialkylsiloxy group having 3 to 10 carbon atoms, a trialkylsilyl group having 3 to 10 carbon atoms, or a phenyl group, and a preferable aspect thereof is similar to that of $R^{12}$, $R^{13}$, and $R^{14}$.

Specific examples of the azo compound (1A) include compounds represented by the following formulas (1-1) to (1-105), but the present invention is not limited thereto.
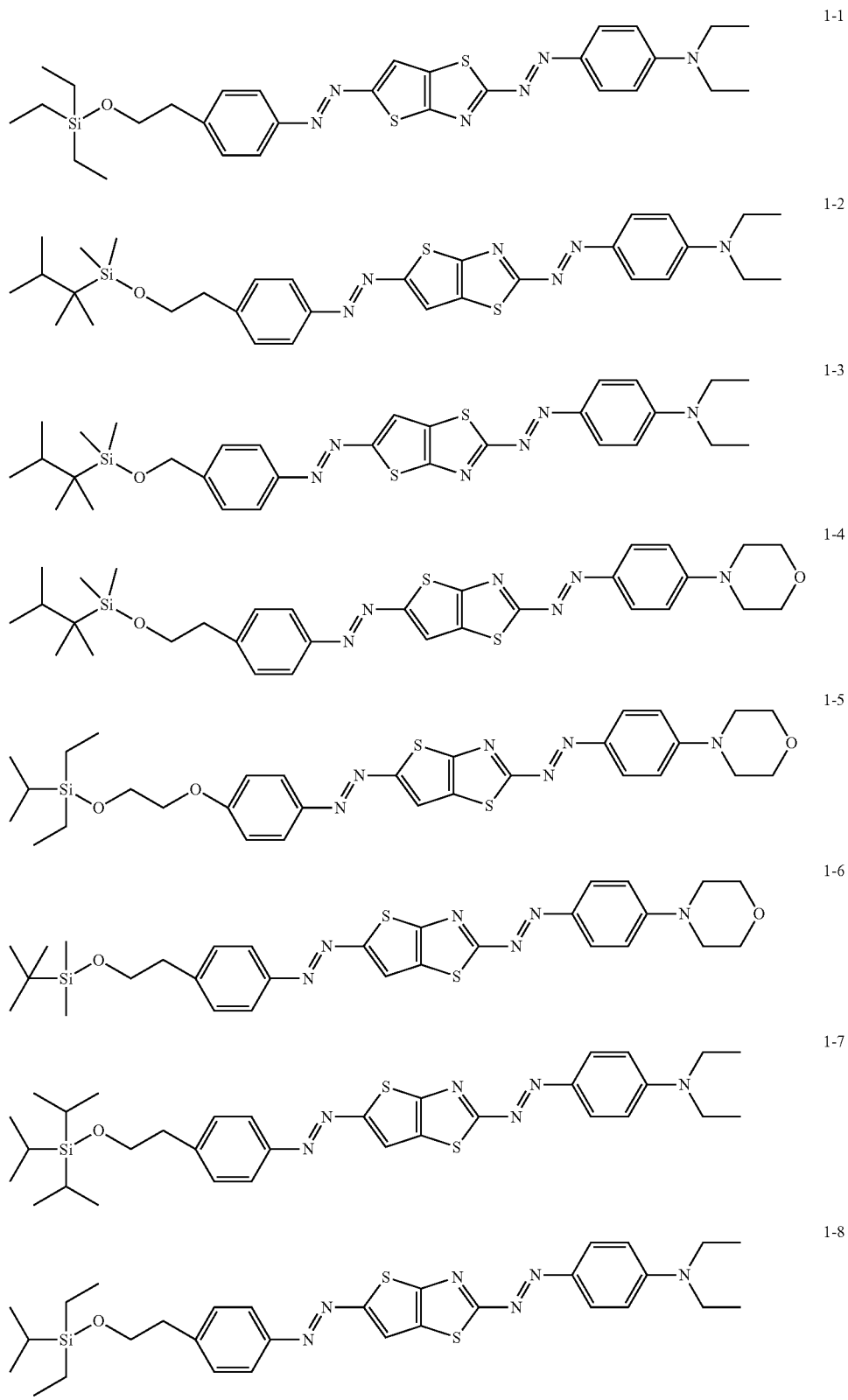

-continued
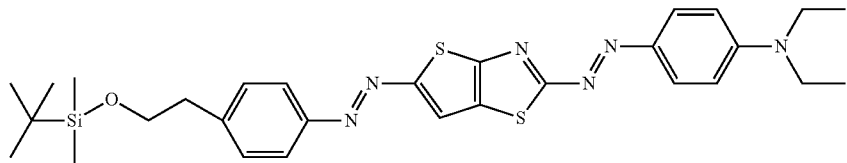
1-9
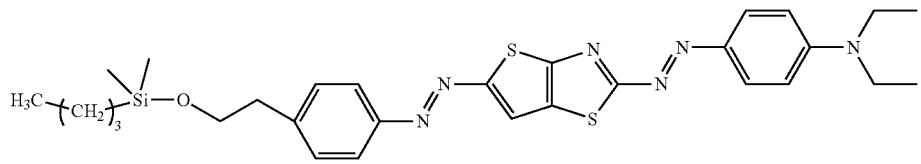
1-10
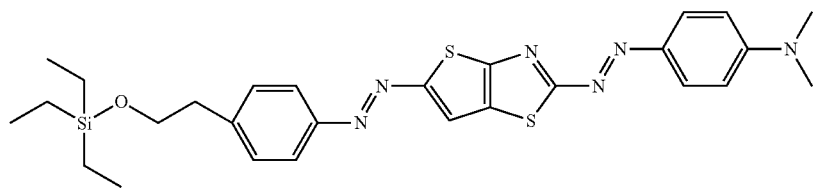
1-11
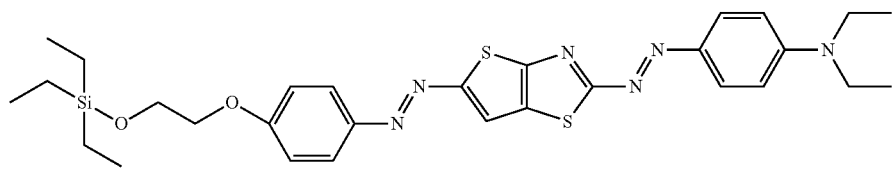
1-12
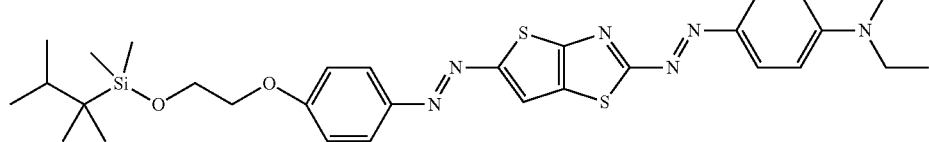
1-13
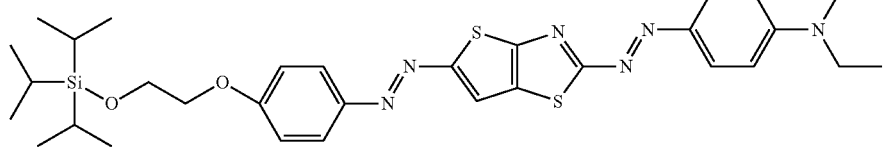
1-14
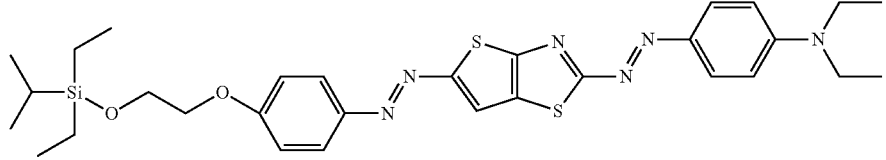
1-15
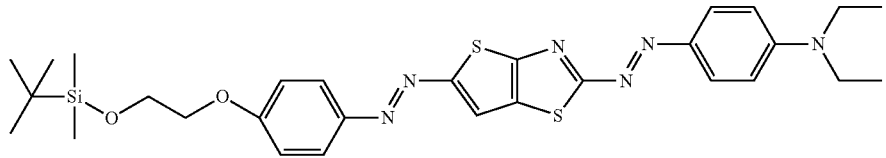
1-15
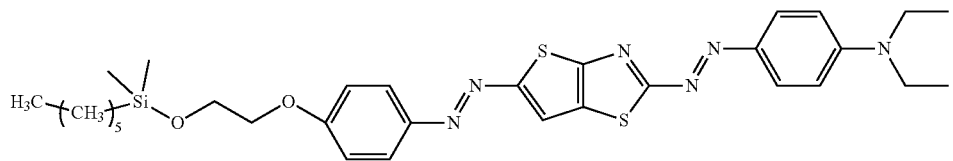
1-16

-continued
1-17
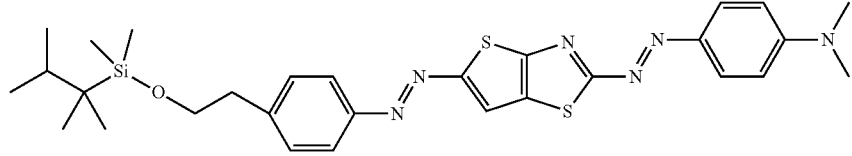
1-18
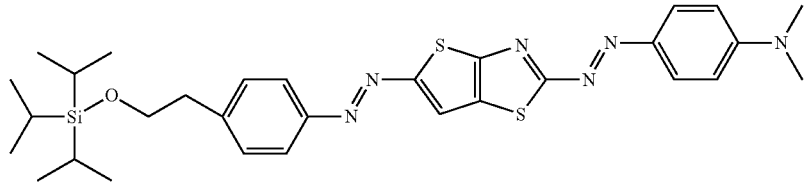
1-19
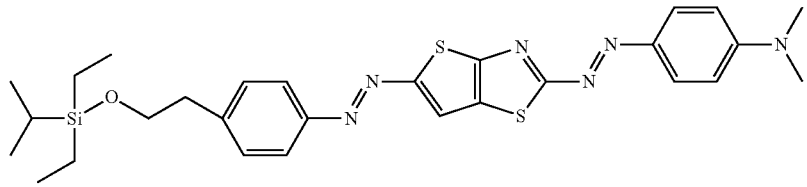
1-20
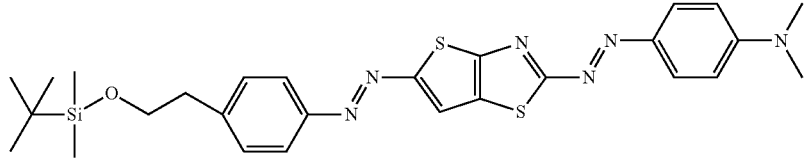
1-21
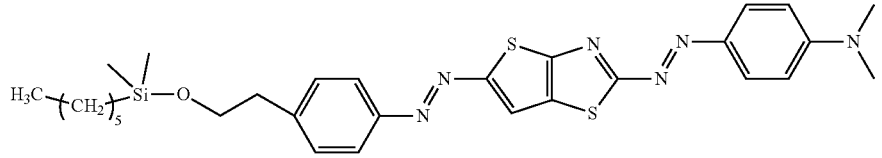
1-22
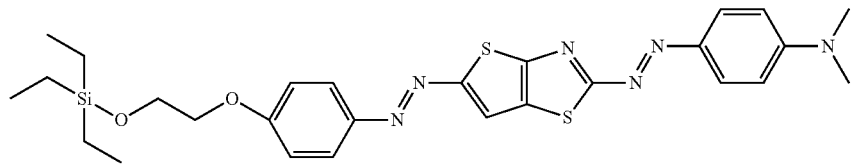
1-23
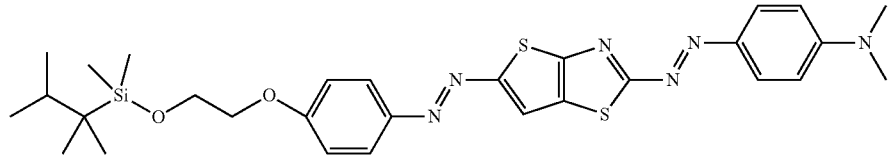
1-24
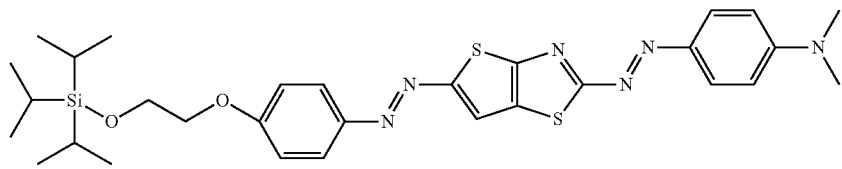
1-25
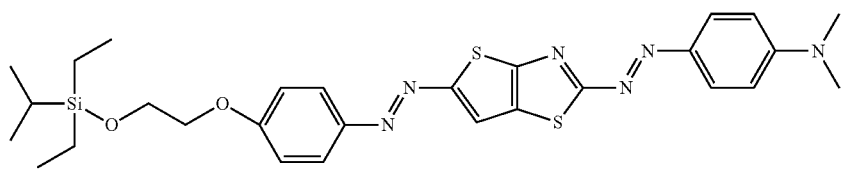

-continued
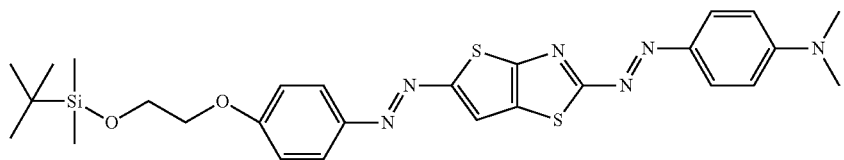
1-26
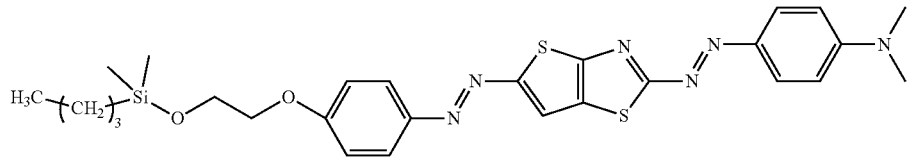
1-27
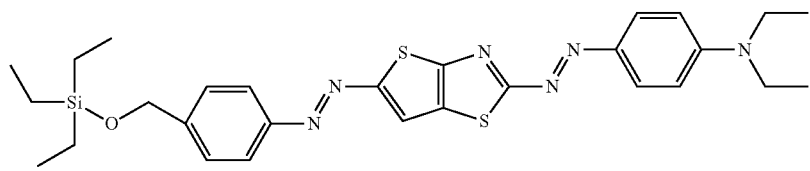
1-28
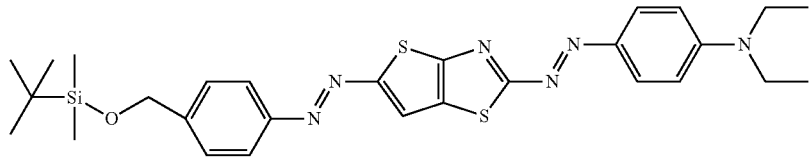
1-29
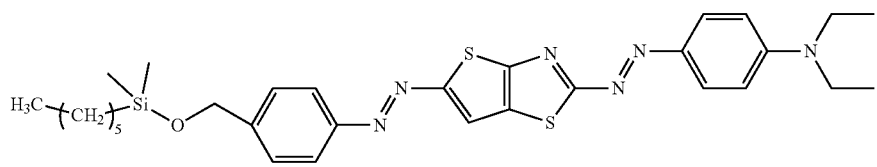
1-30
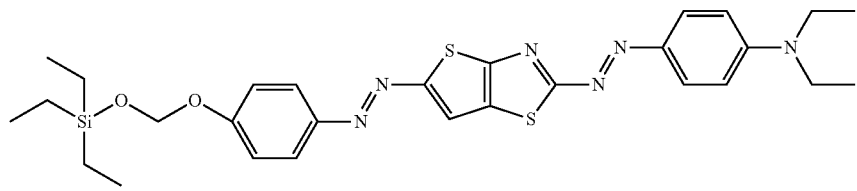
1-31
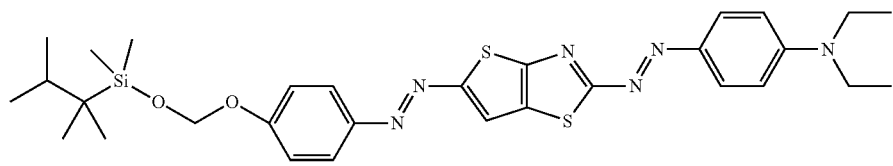
1-32
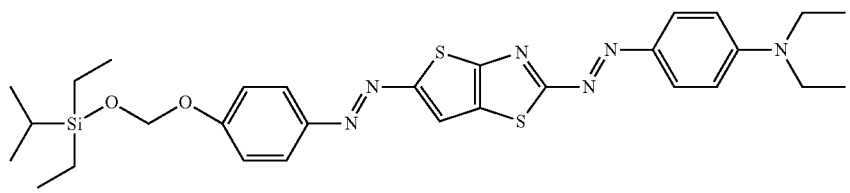
1-33
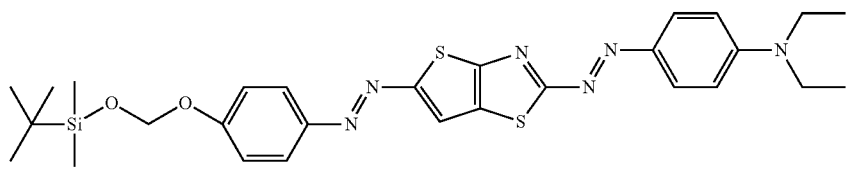
1-34

-continued
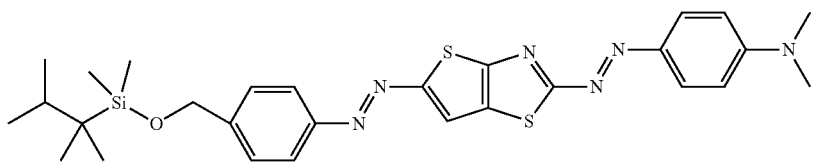
1-35
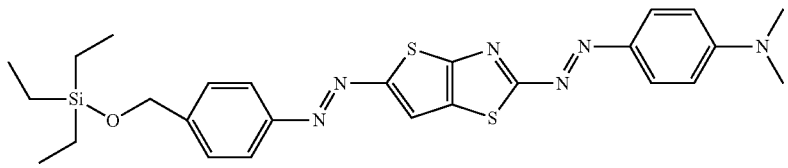
1-36
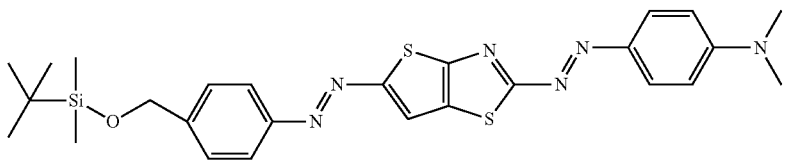
1-37
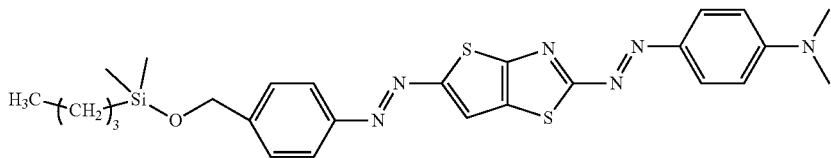
1-38
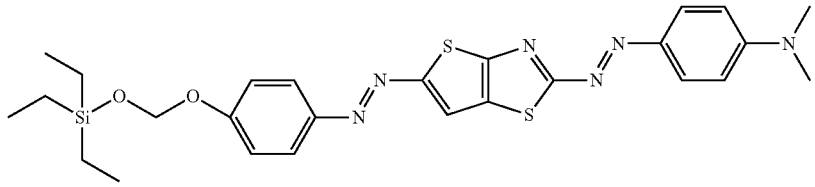
1-39
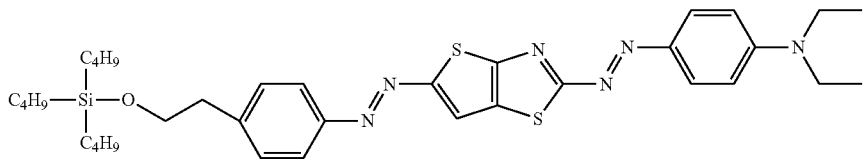
1-40
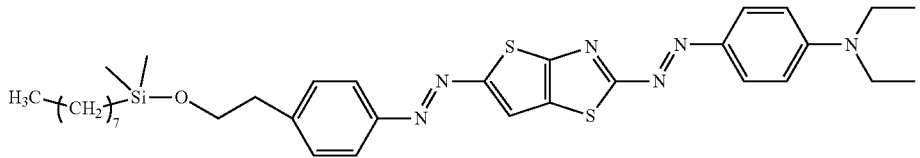
1-41
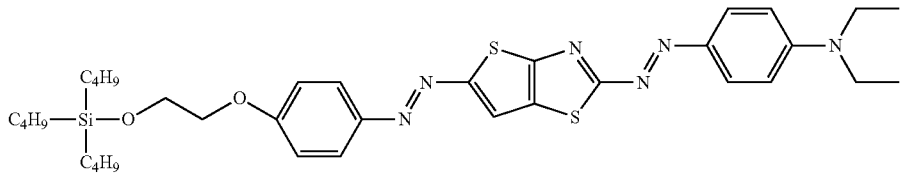
1-42
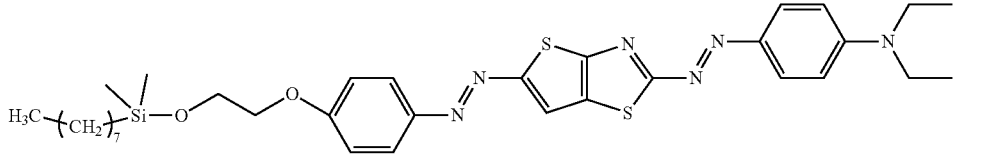
1-43

-continued
1-44
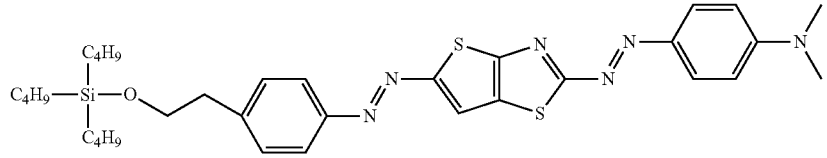
1-45
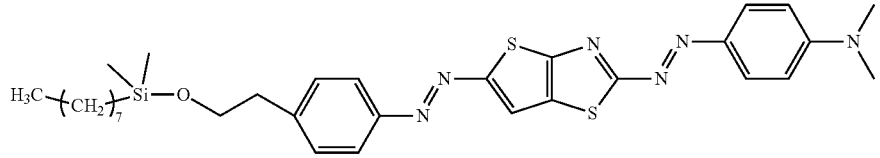
1-46
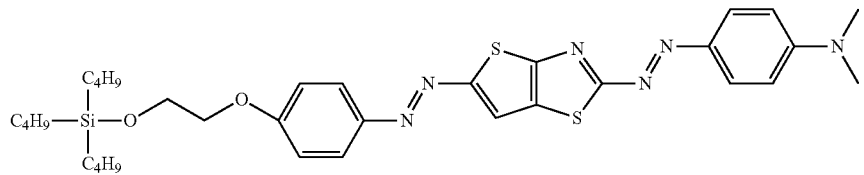
1-47
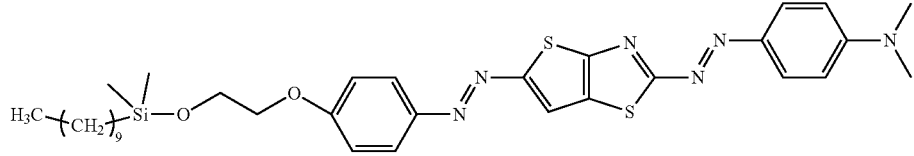
1-48
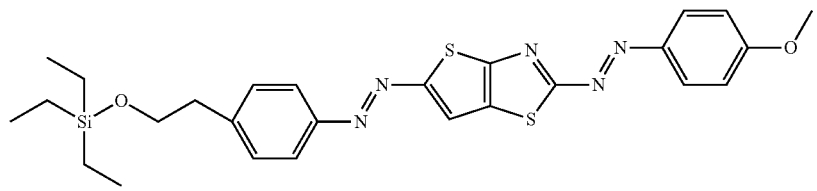
1-49
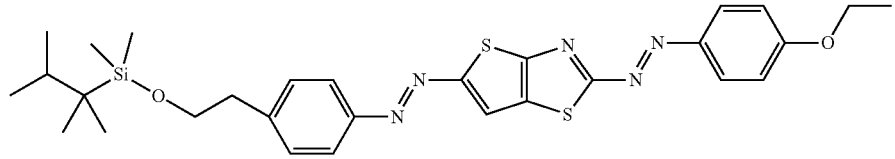
1-50
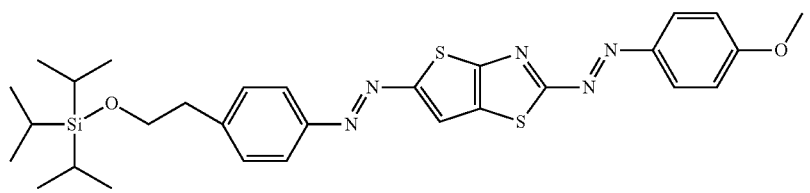
1-51
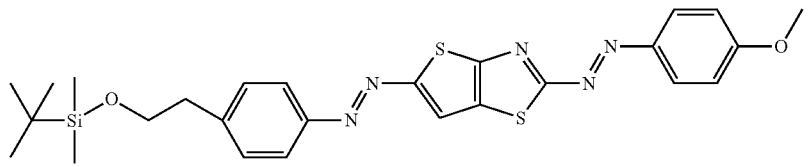
1-52
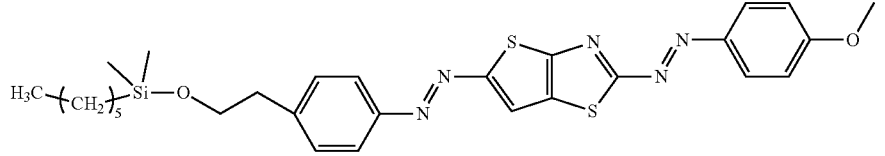

-continued
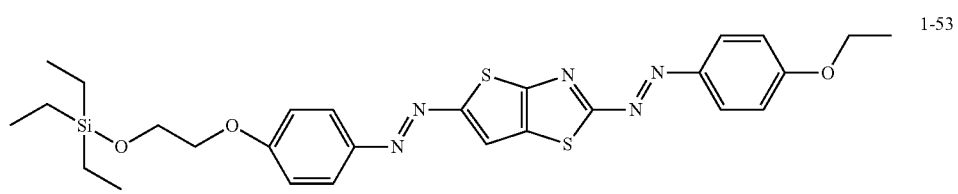
1-53
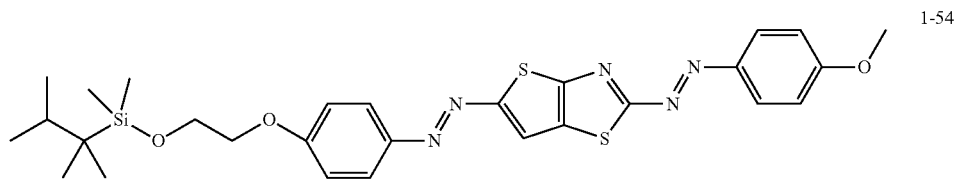
1-54
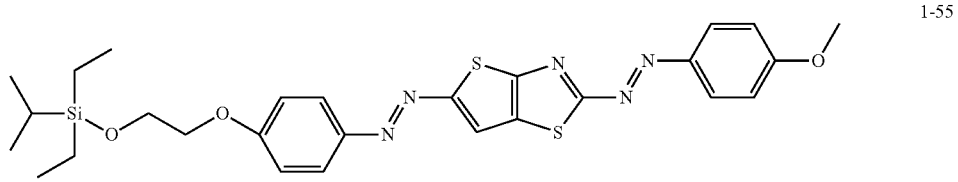
1-55
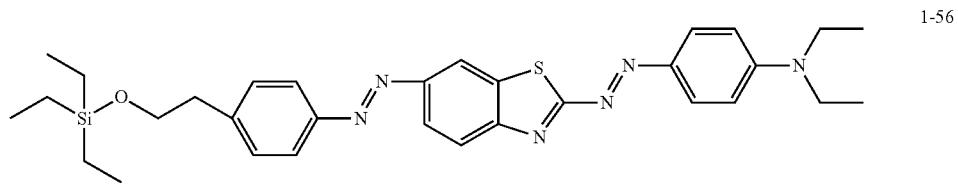
1-56
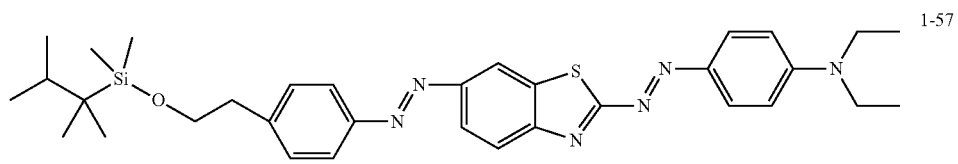
1-57
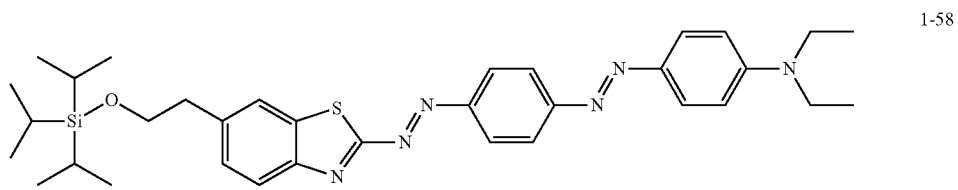
1-58
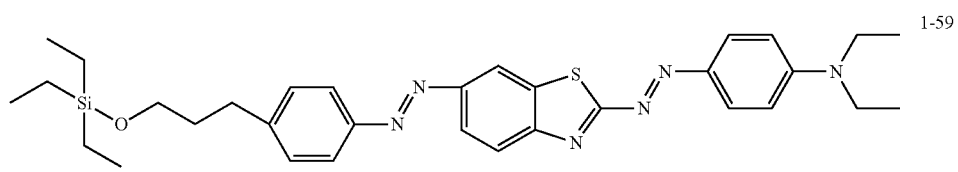
1-59
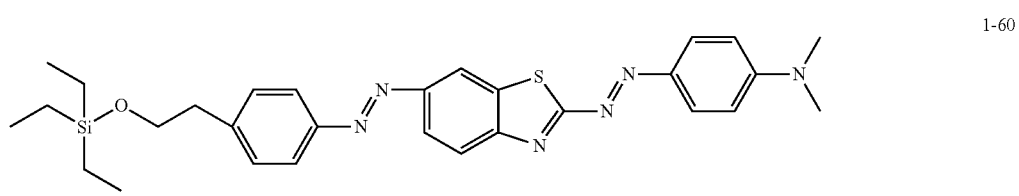
1-60
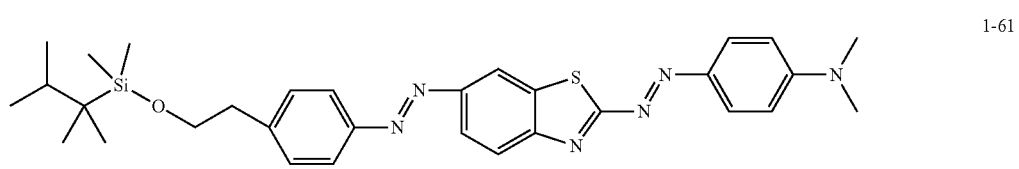
1-61

-continued
1-62
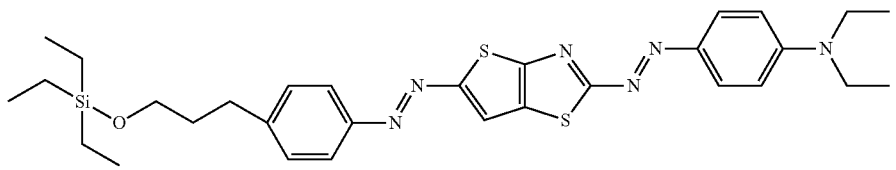
1-63
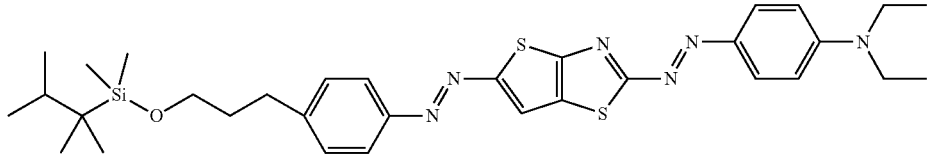
1-64
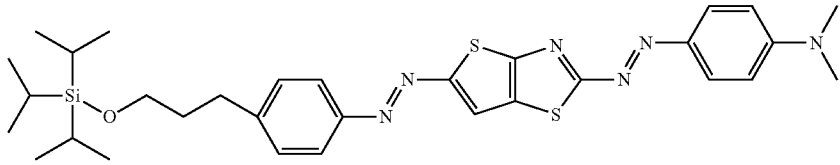
1-65
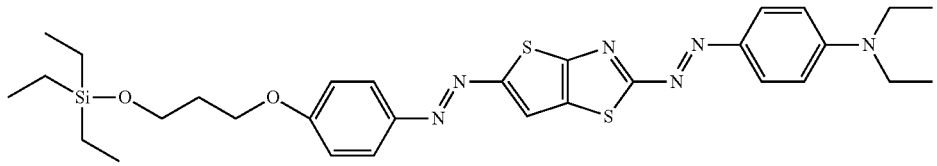
1-66
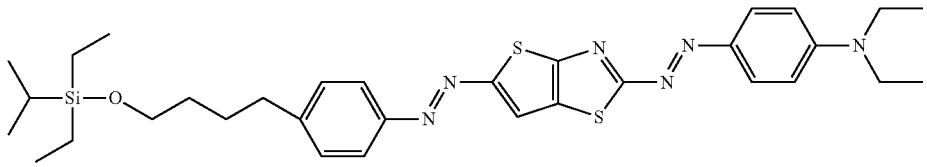
1-67
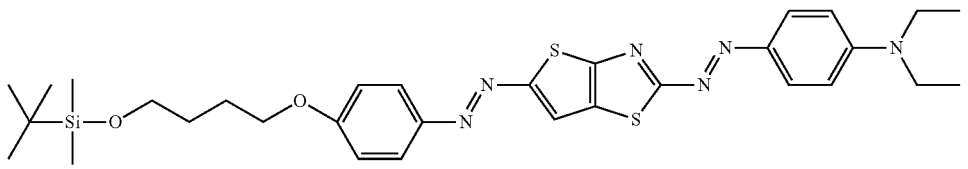
1-68
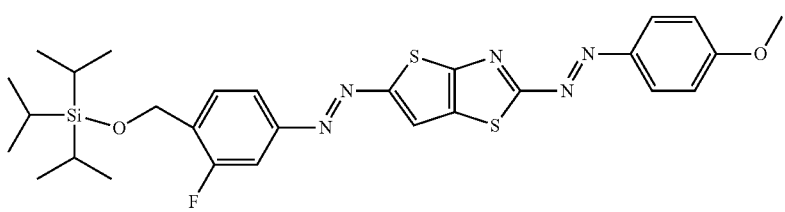
1-69
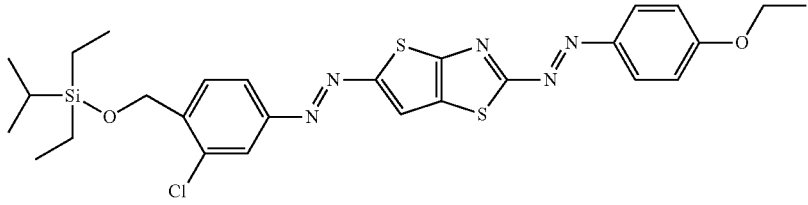
1-70
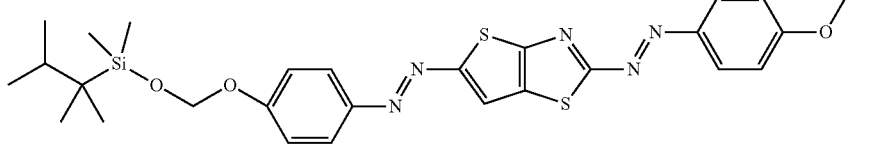

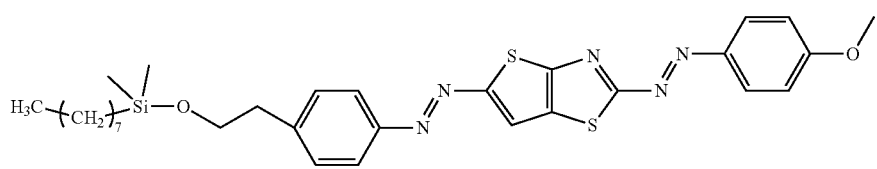
1-71
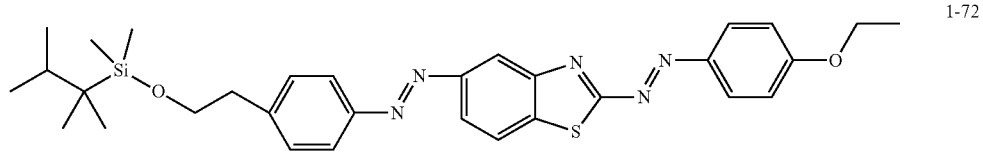
1-72
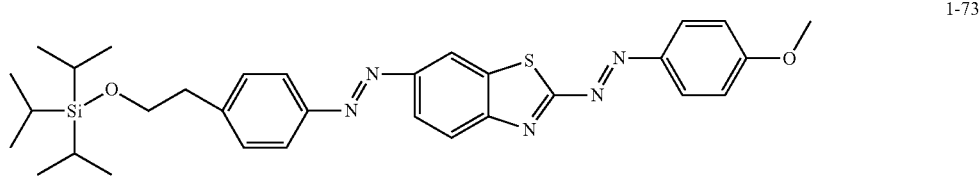
1-73
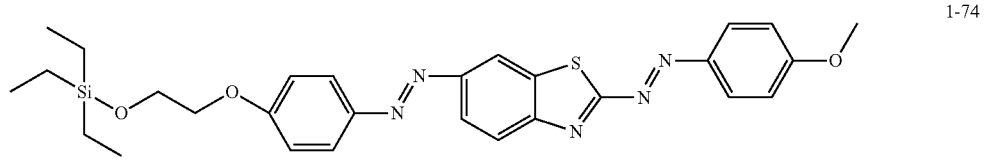
1-74
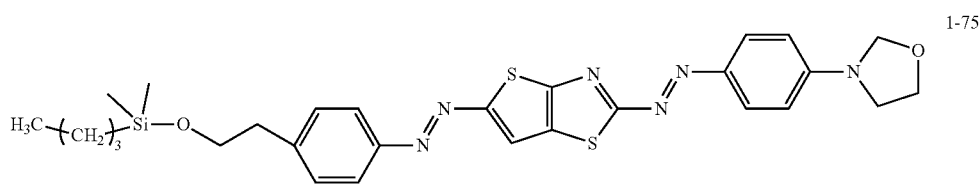
1-75
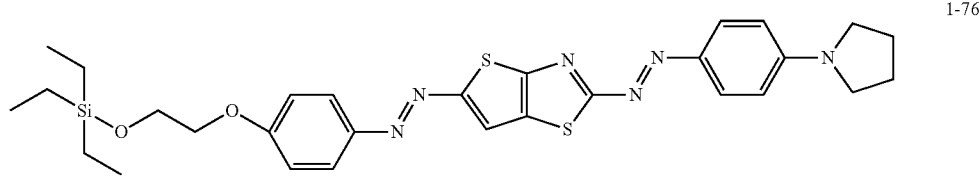
1-76
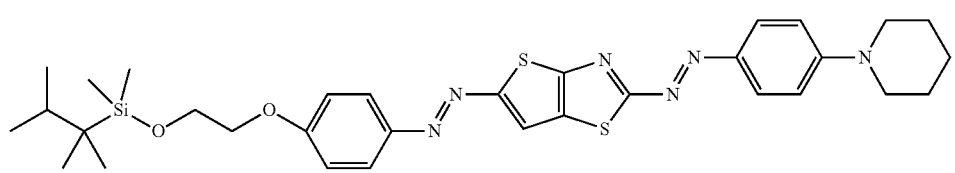
1-77
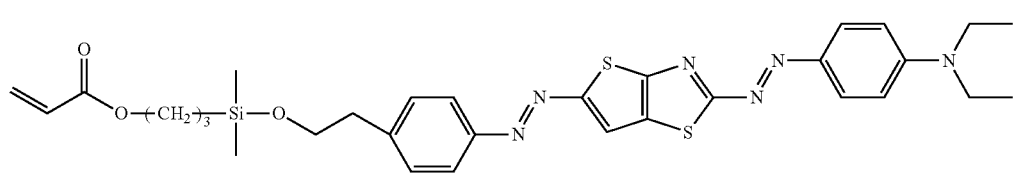
1-78
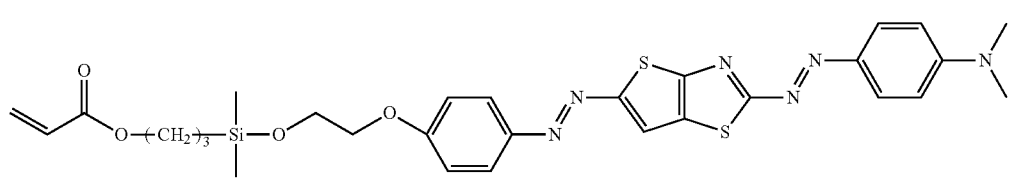
1-79

-continued
1-80
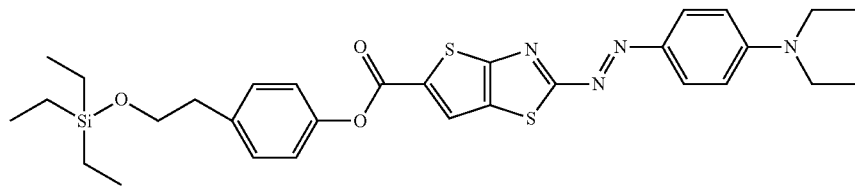
1-81
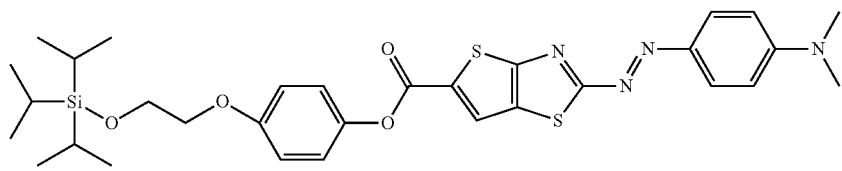
1-82
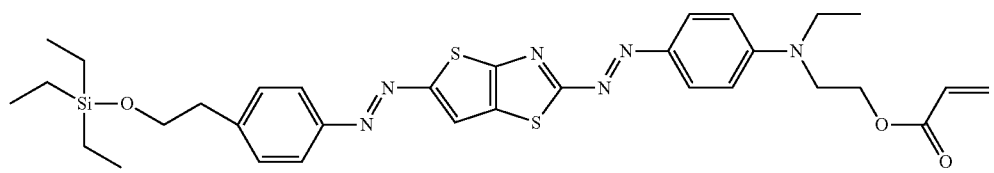
1-83
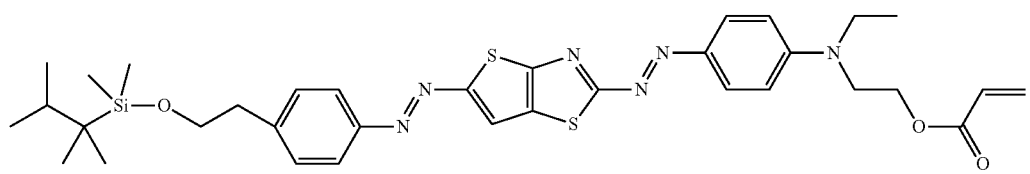
1-84
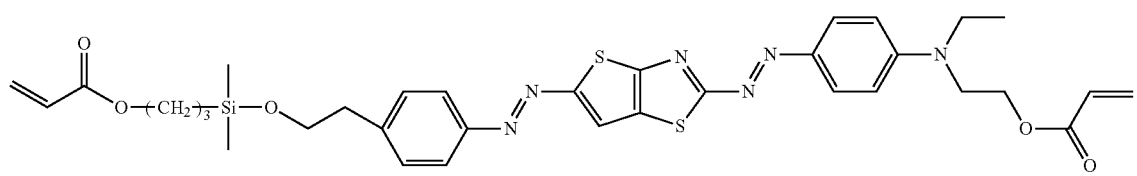
1-85
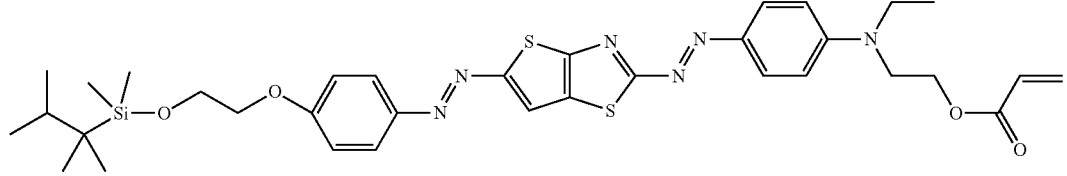
1-86
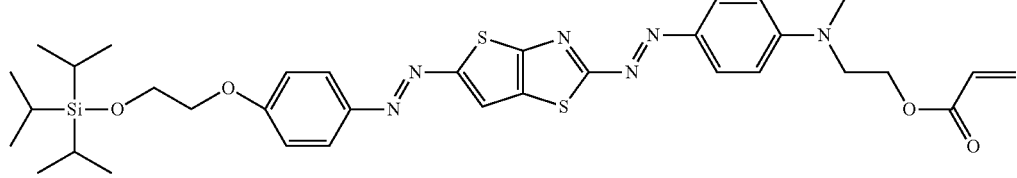
1-87
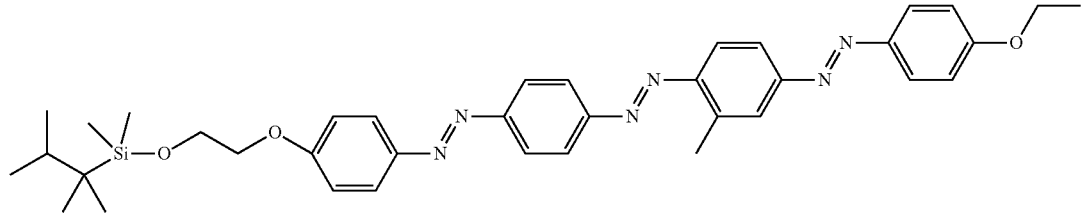

1-88
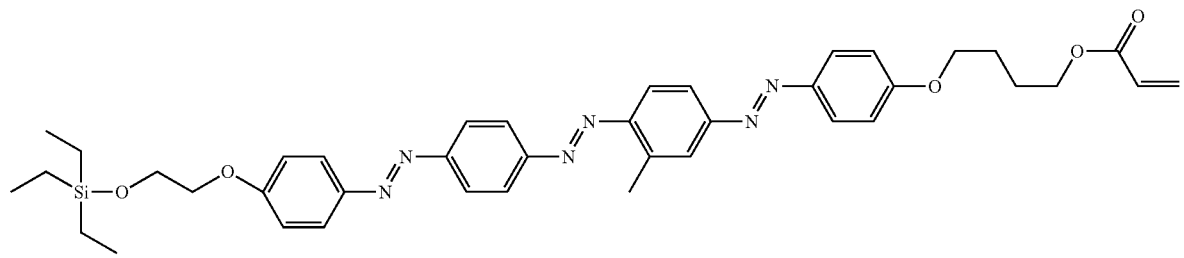
1-89
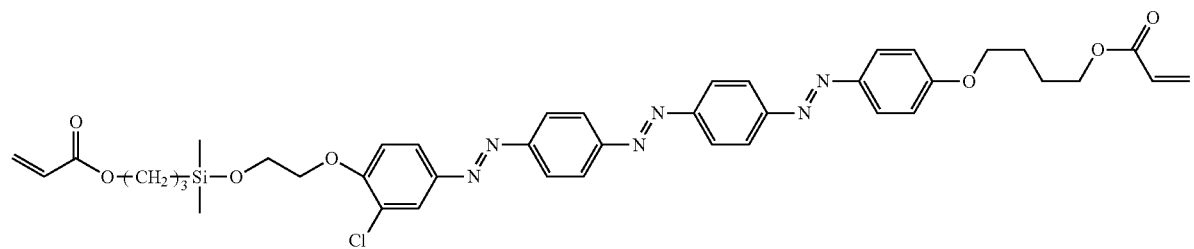
1-90
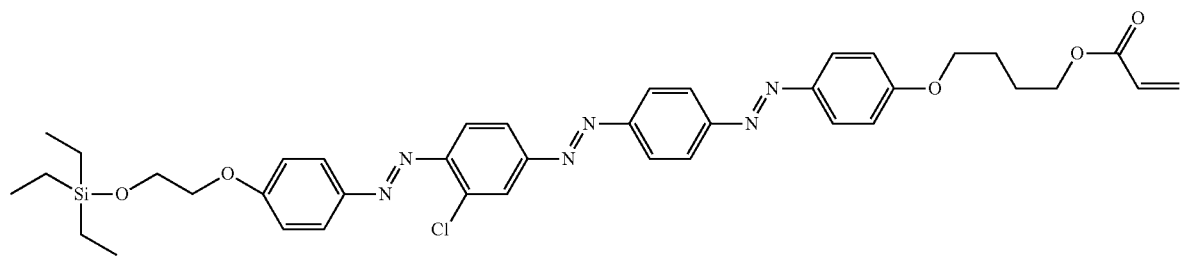
1-91
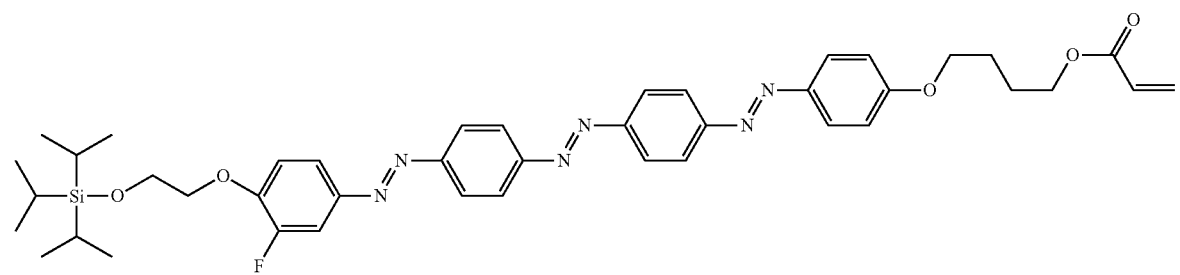
1-92
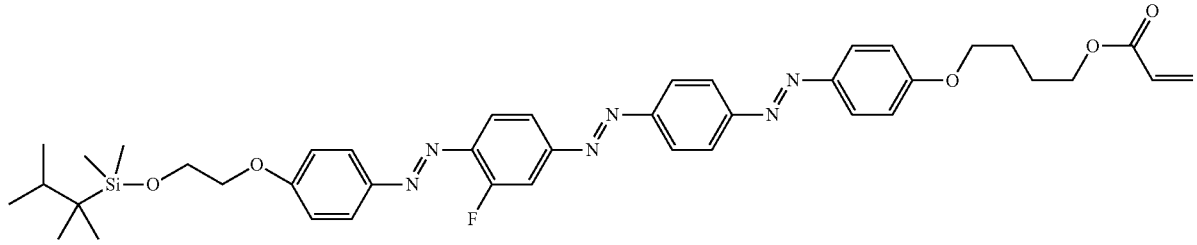

-continued
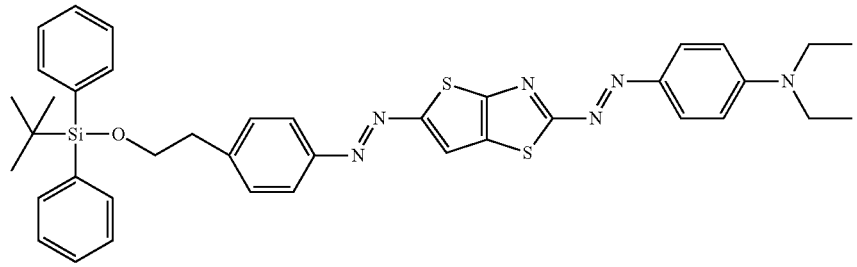
1-93
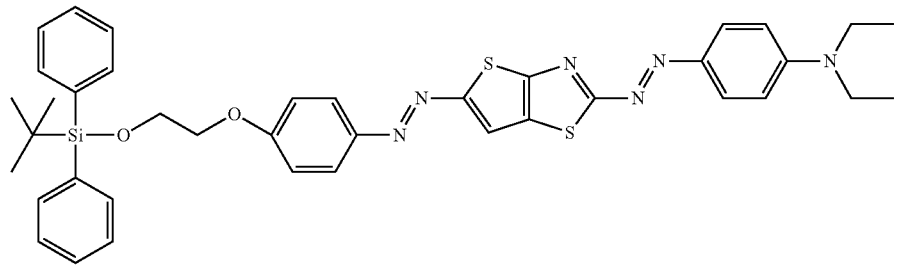
1-94
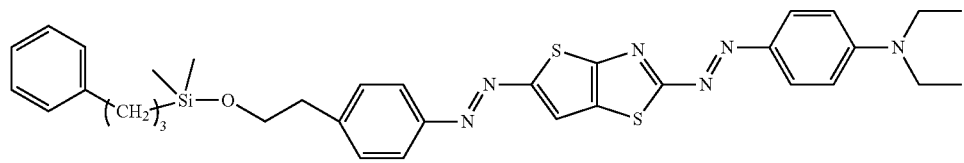
1-95
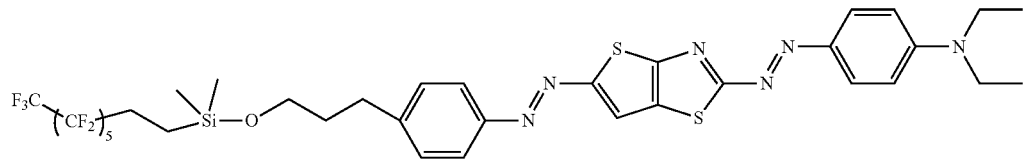
1-96
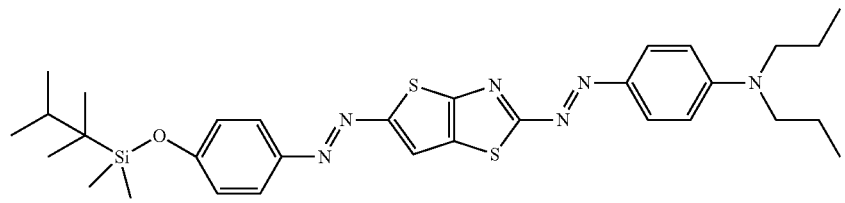
1-97
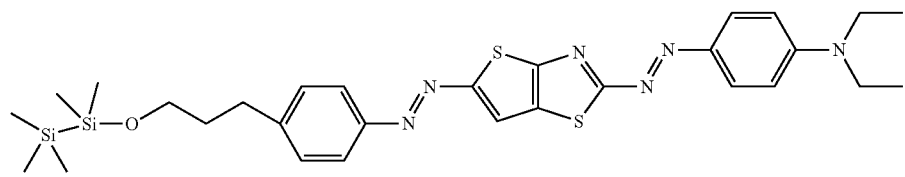
1-98
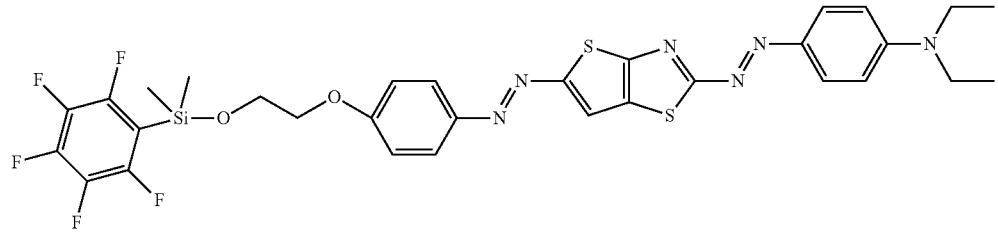
1-99

-continued
1-100
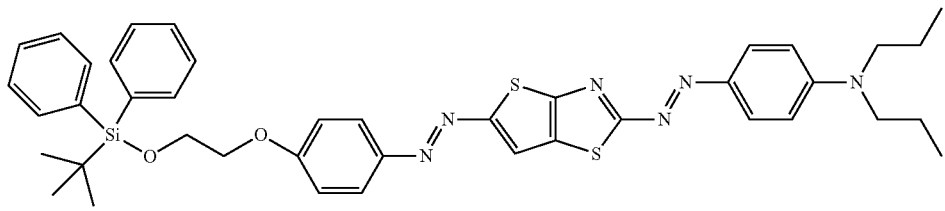
1-101
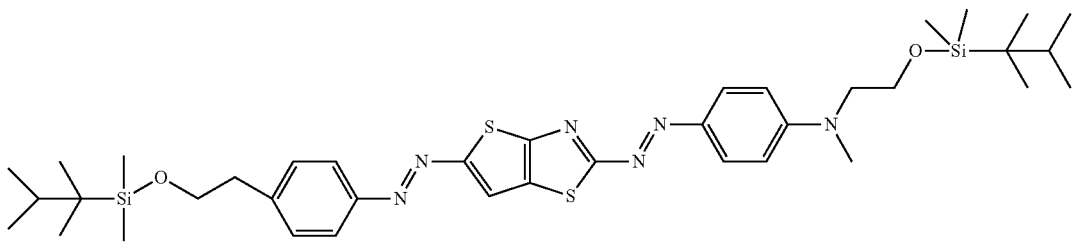
1-102
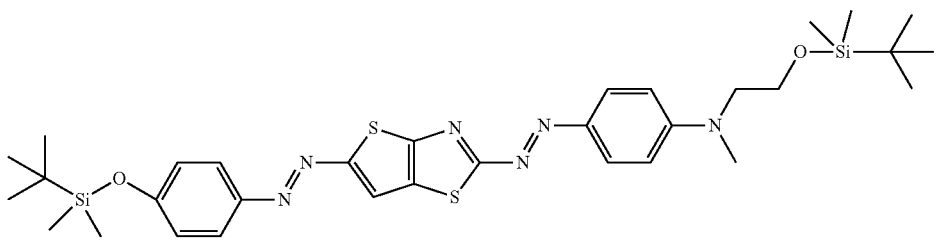
1-103
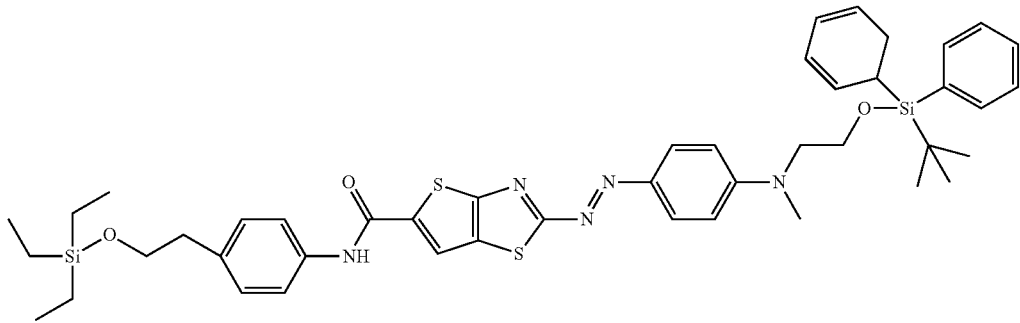
1-104
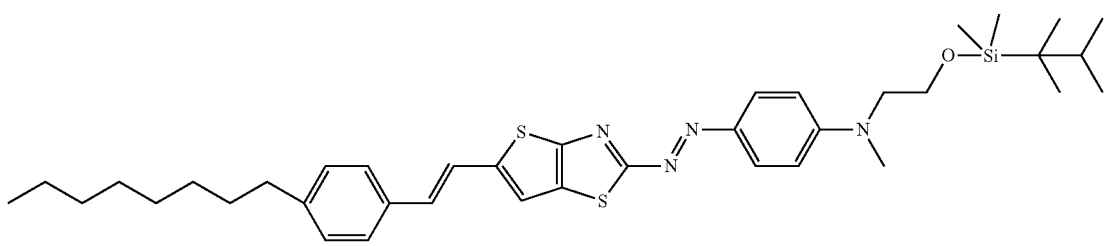
1-105
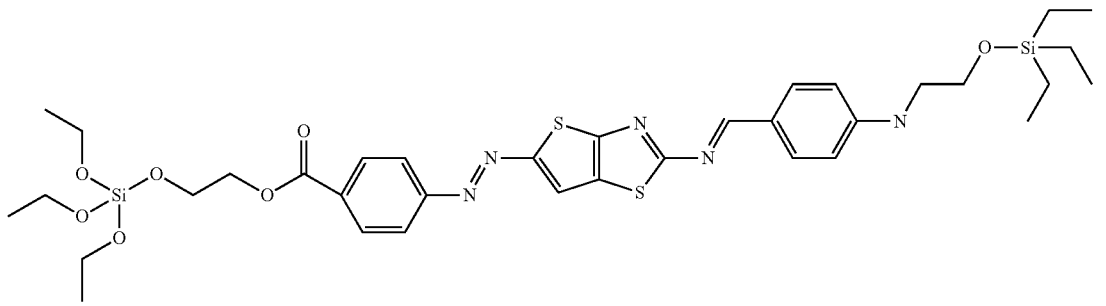

The azo compound (1A) is preferably at least one selected from the group consisting of compounds represented by any of formulas (1-1) to (1-81) and (1-93) to (1-105), more preferably at least one selected from the group consisting of compounds represented by any of formulas (1-1) to (1-67), and particularly preferably at least one selected from the group consisting of compounds represented by any of formulas (1-1), (1-2) and (1-7) to (1-27) from a viewpoint of stability as a composition.

The azo compound (1A) may have a maximum absorption wavelength (λmax) in a wavelength range of, for example, 550 nm or more and 650 nm or less. The maximum absorption wavelength of the azo compound (1A) may be preferably 560 nm or more and 640 nm or less, and more preferably 570 nm or more and 630 nm or less. The maximum absorption wavelength is measured at room temperature (for example, 25° C.) for a chloroform solution of the azo compound (1A). The maximum absorption wavelength of the azo compound (1A) can be adjusted to a desired wavelength by appropriately selecting, for example, skeleton structures of $Ar^1$, $Ar^2$, and $Ar^3$, substituents in $Ar^1$, $Ar^2$, and $Ar^3$, y, and $R^1$.

Since the azo compound (1A) has a specific structure, for example, solubility stability in a solvent is improved, and stability as a composition is improved. This can be considered as follows, for example. A silyloxy group having an aliphatic hydrocarbon group as a substituent is relatively bulky and polar. As a result, it is considered that interaction between molecules of the azo compound (1A) is suppressed, solubility stability in a solvent is improved, and good compatibility with a host can be exhibited. In addition, it is considered that since the silyloxy group is bonded to a chromophore via the linking group L, orientation of the chromophore is not inhibited, and for example, when a polarizing film is formed, a good dichroic ratio (DR) can be maintained.

Method for Producing Azo Compound

The azo compound (1A) can be produced by appropriately applying a conventionally known synthesis method. Specifically, an azo structure (—N═N—) in the azo compound (1A) can be constructed, for example, by converting an aromatic amine compound having a primary amino group into a diazonium salt with sodium nitrite or the like and diazo-coupling the diazonium salt with an aromatic compound with reference to description of production examples in paragraphs [0220] to [0268] of WO-A-2016/136561.

A compound in which Q in the azo compound (1A) is a single bond can by synthesized, for example, by applying reaction conditions of Suzuki coupling with reference to Netherton, M. R.; Fu, G. C. Org. Lett. 2001, 3 (26), 4295-4298 and the like using a precursor having a dihydroxyboryl group or a dialkoxyboryl group and a precursor having a halogen atom.

A compound in which Q in the azo compound (1A) is —OC(═O)— or C(═O)O— can by synthesized, for example, by applying a dehydration condensation reaction with reference to Jiang, L.; Lu, X.; Zhang, H.; Jiang, Y.; Ma, D. J. Org. Chem. 2009, 74 (3), 4542-4546 and the like using a precursor having a carboxy group and a precursor having a hydroxy group. Specific examples thereof include conditions for condensation in a solvent in the presence of an esterification condensing agent.

A compound in which Q in the azo compound (1A) is —C≡C— can by synthesized, for example, by applying Sonogashira coupling using a Pd catalyst and a Cu catalyst using a precursor having an ethynyl group (—C≡CH) and a precursor having a halogen atom.

A compound in which Q in the azo compound (1A) is —C═C— can by synthesized, for example, by applying a Heck reaction using a Pd catalyst and a phosphorus ligand using a precursor having an ethenyl group (—C═CH) and a precursor having a halogen atom.

A compound in which Q in the azo compound (1A) is —NHC(═O)— or C(═O)NH— can be synthesized, for example, by applying a dehydration condensation reaction using a precursor having a carboxy group and a precursor having an amino group. Specific examples thereof include conditions for condensation in a solvent in the presence of an amidation condensing agent.

The silyloxy group having an aliphatic hydrocarbon group as a substituent in the azo compound (1A) can be synthesized by applying conditions of a general silylation reaction in the presence of a base using a precursor having a hydroxy group and a halogenated silane having an aliphatic hydrocarbon group as a substituent. For conditions of a $S_N 2$ substitution reaction, for example, J. Am. Chem. Soc., 1972, 94, 6190 can be referred to.

Reaction time in the method for producing the azo compound (1A) can also be determined by appropriately sampling a reaction mixture in the middle of the reaction and confirming the degree of disappearance of a raw material compound, the degree of generation of the azo compound (1A), and the like by a known analysis means such as liquid chromatography or gas chromatography.

From the reaction mixture after the reaction, the azo compound (1A) can be extracted by a known method such as recrystallization, reprecipitation, extraction, or various kinds of chromatography, or by appropriately combining these operations.

<Dichroic Dye>

The dichroic dye contains at least one kind of azo compound (1A) as an active ingredient. By containing the azo compound (1A), the dichroic dye can form a polarizing film in which generation of orientation defects is suppressed. The dichroic dye may contain only one kind of azo compound (1A), or may contain two or more kinds of azo compounds (1A) having different structures in combination. When the dichroic dye contains two or more kinds of azo compounds (1A), the azo compounds (1A) may have mutually different maximum absorption wavelengths. The dichroic dye may contain, in addition to the azo compound (1A), another dye compound other than the azo compound (1A). The other dye compound will be described later.

<Composition>

A composition of the present embodiment contains at least one kind of azo compound (1A), and a liquid crystalline compound containing at least one of a polymerizable liquid crystal compound and a liquid crystalline polymer compound. The composition is used, for example, as a material for forming a polarizing film. That is, the composition may be a composition for forming a polarizing film. A polarizing film obtained by using the composition as a forming material is a high-quality polarizing film in which generation of orientation defects is suppressed while maintaining an excellent dichroic ratio. Since the composition contains the azo compound (1A) as a dichroic dye, the composition can form a polarizing film which has excellent stability as a composition even after storage for a predetermined time and in which generation of orientation defects is suppressed.

The content of the azo compound (1A) in the composition is, for example, preferably 50 parts by mass or less, more preferably 0.1 parts by mass or more and 10 parts by mass or less, and still more preferably 0.1 parts by mass or more and 5 parts by mass or less based on 100 parts by mass of the solid matter of the composition. Within the above range, the azo compound (1A) can be dispersed sufficiently. As a result, it is possible to efficiently obtain a film containing the azo compound (1A) as a forming material and sufficiently suppressing generation of defects. Note that in the present specification, the solid matter refers to the total amount of components excluding a volatile component such as a solvent from the composition. The composition may contain only one kind of azo compound (1A), or may contain two or more kinds of azo compounds (1A) having different structures in combination. When the composition contains two or more kinds of azo compounds (1A), the azo compounds (1A) may have mutually different maximum absorption wavelengths.

The composition may further contain another dye compound other than the azo compound (1A), for example, at least one kind of dichroic dye. Examples of the other dye compound include an azo dye such as a monoazo dye, a bisazo dye, a trisazo dye, a tetrakis azo dye, or a stilbene azo dye, and at least one selected from the group consisting of these dyes is preferable. The composition may contain the other dye compound singly or in combination of two or more kinds thereof. For example, when the composition is used as an application type polarizing plate material, the other dye compound contained in the composition preferably has a maximum absorption wavelength in a wavelength range different from that of the azo compound (1A). For example, when the composition is used as an application type polarizing plate material, the composition preferably contains three or more kinds of dichroic dyes in combination, and more preferably contains three or more kinds of azo dyes in combination, including the azo compound (1A). When the composition contains three or more kinds of dye compounds having different maximum absorption wavelengths in combination, for example, absorption can be obtained in the entire visible light region by a film formed from the composition.

When the composition contains the other dye compound, the content of the other dye compound is preferably 50 parts by mass or less, more preferably 0.1 parts by mass or more and 10 parts by mass or less, and still more preferably 0.1 parts by mass or more and 5 parts by mass or less based on 100 parts by mass of the solid matter of the composition. Within the above range, the other dye compound can be dispersed sufficiently.

The composition contains, in addition to the azo compound (1A), a liquid crystalline compound containing at least one of a polymerizable liquid crystal compound and a liquid crystalline polymer compound. The composition may contain both a polymerizable liquid crystal compound and a liquid crystalline polymer compound. Two or more kinds of polymerizable liquid crystal compounds and two or more kinds of liquid crystalline polymer compounds may be contained in the composition. When the composition contains at least one of a polymerizable liquid crystal compound and a liquid crystalline polymer compound, it is possible to constitute a composition in which the azo compound (1A) is dispersed in the liquid crystalline compound.

The liquid crystalline polymer compound may constitute a thermotropic liquid crystal type polymer or a lyotropic liquid crystal type polymer. The liquid crystalline polymer compound preferably constitutes a thermotropic liquid crystal type polymer in that the liquid crystalline polymer compound constituting a thermotropic liquid crystal type polymer can accurately control a film thickness.

The liquid crystal is classified into a smectic liquid crystal, a nematic liquid crystal, and a cholesteric liquid crystal depending on the structure of a molecular arrangement in a liquid crystal state. Among these liquid crystals, a smectic liquid crystal is preferably used in an application for a polarizing film. Therefore, the polymerizable liquid crystal compound is preferably a polymerizable smectic liquid crystal compound, and the liquid crystalline polymer compound is preferably a smectic liquid crystalline polymer compound.

By using a polymerizable liquid crystal compound exhibiting smectic liquid crystallinity and a polymer compound exhibiting smectic liquid crystallinity, a polarizing film having a high degree of orientation order can be formed. The liquid crystal state exhibited by the polymerizable liquid crystal compound and the liquid crystalline polymer compound is preferably a smectic phase (smectic liquid crystal state), and more preferably a high-order smectic phase (high-order smectic liquid crystal state) from a viewpoint of being able to achieve a higher degree of orientation order. Here, the high-order smectic phase means a smectic B phase, a smectic D phase, a smectic E phase, a smectic F phase, a smectic G phase, a smectic H phase, a smectic I phase, a smectic J phase, a smectic K phase, and a smectic L phase. Among these phases, a smectic B phase, a smectic F phase, and a smectic I phase are more preferable. A polarizing film having a high degree of orientation order obtains a Bragg peak derived from a high-order structure such as a hexatic phase or a crystal phase in X-ray diffractometry. The Bragg peak means a peak derived from a plane periodic structure of molecular orientation. A periodic interval (order period) of a polarizing film obtained from the composition is preferably 0.3 nm or more and 0.6 nm or less. The polymerizable liquid crystal compound or the liquid crystalline polymer compound may be a polymerizable smectic liquid crystal compound or a smectic liquid crystalline polymer compound that exhibits a Bragg peak derived from a high-order structure in X-ray diffractometry.

The azo compound (1A) can exhibit high dichroism even in a state of being dispersed between dense molecular chains formed from at least one of a smectic liquid crystalline polymerizable liquid crystal compound and a smectic liquid crystalline polymer compound. Therefore, a composition containing the azo compound (1A) and a liquid crystalline compound containing at least one of a polymerizable liquid crystal compound and a liquid crystalline polymer compound, particularly a liquid crystalline compound containing at least one of a smectic liquid crystalline polymerizable liquid crystal compound and a smectic liquid crystalline polymer compound can provide a polarizing film in which generation of orientation defects is suppressed and which has a high dichroic ratio.

Polymerizable Liquid Crystal Compound

The polymerizable liquid crystal compound is a compound having at least one polymerizable group in a molecule thereof and capable of exhibiting a liquid crystal phase by being orientated. The polymerizable liquid crystal compound is preferably a compound capable of exhibiting a liquid crystal phase by being orientated alone. The polymerizable group means a functional group that can be involved in a polymerization reaction, and is preferably a radically polymerizable group.

The polymerizable liquid crystal compound is not particularly limited as long as the polymerizable liquid crystal compound is a liquid crystal compound having at least one polymerizable group and preferably exhibiting smectic liquid crystallinity, and a known polymerizable liquid crystal compound can be used. Specific preferable examples of the polymerizable liquid crystal compound include a compound represented by the following formula (A) (hereinafter, also referred to as "polymerizable liquid crystal compound (A)"):

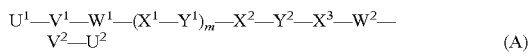

$$U^1-V^1-W^1-(X^1-Y^1)_m-X^2-Y^2-X^3-W^2-V^2-U^2 \quad (A)$$

In formula (A), m is an integer of 1 to 3. $X^1$, $X^2$, and $X^3$ each independently represent a divalent aromatic group or a divalent alicyclic hydrocarbon group. When m is 2 or 3, a plurality of $X^1$s may be the same as or different from each other. At least three selected from the group consisting of $X^1$, $X^2$, and $X^3$ each represent a divalent hydrocarbon six-membered ring group. $Y^1$, $Y^2$, $W^1$, and $W^2$ each independently represent a single bond or a divalent linking group. When m is 2 or 3, a plurality of $Y^1$s may be the same as or different from each other. $V^1$ and $V^2$ each independently represent an alkanediyl group having 1 to 20 carbon atoms and optionally having a substituent. At least one of —$CH_2$-s constituting the alkanediyl group may be replaced with —O—, —CO—, —S—, or —NH—. $U^1$ and $U^2$ each independently represent a polymerizable group or a hydrogen atom, and at least one of $U^1$ and $U^2$ represents a polymerizable group.

Examples of the divalent aromatic group in $X^1$, $X^2$, and $X^3$ include a 1,4-phenylene group and a 1,4-naphthylene group. Examples of the divalent alicyclic hydrocarbon group include a cyclohexane-1,4-diyl group. At least one of the divalent aromatic group and the divalent alicyclic hydrocarbon group in $X^1$, $X^2$, and $X^3$ optionally has a substituent. Examples of the substituent include an alkyl group having 1 to 4 carbon atoms, such as a methyl group, an ethyl group, or a n-butyl group, a cyano group, and a halogen atom. At least one of —$CH_2$-s constituting the divalent alicyclic hydrocarbon group may be replaced with —O—, —S—, or —NR—. Here, R represents an alkyl group having 1 to 6 carbon atoms or a phenyl group.

Examples of the divalent hydrocarbon six-membered ring group in $X^1$, $X^2$, and $X^3$ include a 1,4-phenylene group optionally having a substituent and a cyclohexane-1,4-diyl group optionally having a substituent.

The divalent aromatic group in $X^1$, $X^2$, and $X^3$ is preferably a 1,4-phenylene group optionally having a substituent, and more preferably an unsubstituted 1,4-phenylene group. In addition, the divalent alicyclic hydrocarbon group is preferably a cyclohexane-1,4-diyl group optionally having a substituent, more preferably a trans-cyclohexane-1,4-diyl group optionally having a substituent, and still more preferably an unsubstituted trans-cyclohexane-1,4-diyl group.

$Y^1$ and $Y^2$ each independently represent a single bond or a divalent linking group. The divalent linking group is, for example, at least one selected from the group consisting of —$CH_2CH_2$—, —$CH_2O$—, —(C=O)O—, —O(C=O)O—, —N=N—, —$CR^a$=$CR^b$—, —C≡C—, and —$CR^a$=N—. Here, $R^a$ and $R^b$ each independently represent a hydrogen atom or an alkyl group having 1 to 4 carbon atoms. $Y^1$ is preferably —$CH_2CH_2$—, —(C=O)O—, or a single bond. $Y^2$ is preferably —$CH_2CH_2$— or —$CH_2O$—.

$W^1$ and $W^2$ each independently represent a single bond or a divalent linking group. The divalent linking group is, for example, at least one selected from the group consisting of —O—, —S—, —(C=O)O—, and —O(C=O)O—. $W^1$ and $W^2$ are each independently preferably a single bond or —O—.

$V^1$ and $V^2$ each independently represent an alkanediyl group having 1 to 20 carbon atoms and optionally having a substituent; at least one of —$CH_2$-s constituting the alkanediyl group may be substituted with —O—, —CO—, —S—, or —NH—; and Examples of the alkanediyl group represented by $V^1$ and $V^2$ include a methylene group, an ethylene group, a propane-1,3-diyl group, a butane-1,3-diyl group, a butane-1,4-diyl group, a pentane-1,5-diyl group, a hexane-1,6-diyl group, a heptane-1,7-diyl group, an octane-1,8-diyl group, a decane-1,10-diyl group, a tetradecane-1,1-diyl group, and an icosane-1,20-diyl group. $V^1$ and $V^2$ are each preferably an alkanediyl group having 2 to 12 carbon atoms, and more preferably an alkanediyl group having 6 to 12 carbon atoms.

Examples of the substituent optionally included in the alkanediyl group having 1 to 20 carbon atoms and optionally having a substituent include a cyano group and a halogen atom. The alkanediyl group is preferably an alkanediyl group having no substituent, and more preferably a linear alkanediyl group having no substituent.

$U^1$ and $U^2$ each independently represent a polymerizable group or a hydrogen atom, and at least one of $U^1$ and $U^2$ represents a polymerizable group. $U^1$ and $U^2$ are preferably polymerizable groups. $U^1$ and $U^2$ are preferably both polymerizable groups, and preferably both radically polymerizable groups. The polymerizable group represented by $U^1$ and the polymerizable group represented by $U^2$ may be different from each other, but are preferably the same kind of group. Examples of the polymerizable groups in $U^1$ and $U^2$ include polymerizable groups similar to those exemplified above as the polymerizable group included in the polymerizable liquid crystal compound. Among these groups, each of the polymerizable groups represented by $U^1$ and $U^2$ is preferably at least one selected from the group consisting of a vinyloxy group, an acryloyloxy group, a methacryloyloxy group, an oxiranyl group, and an oxetanyl group, and more preferably an acryloyloxy group.

Specific examples of polymerizable liquid crystal compound (A) include compounds represented by the following formulas (A-1) to (A-17). When polymerizable liquid crystal compound (A) has a cyclohexane-1,4-diyl group, the cyclohexane-1,4-diyl group is preferably a trans type.

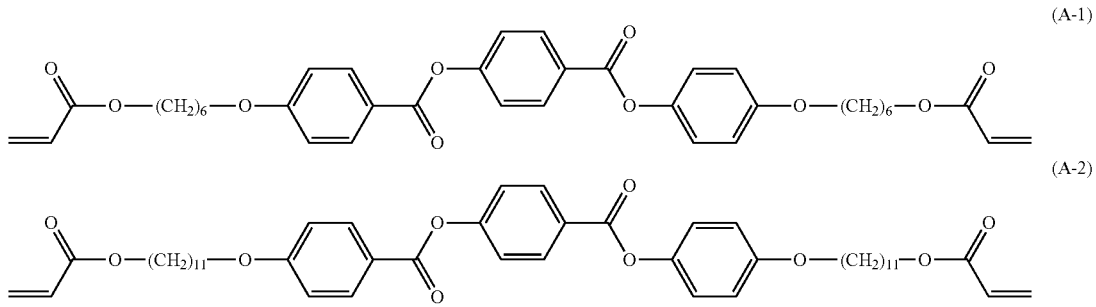

-continued
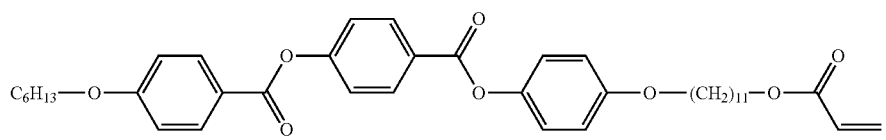
(A-3)
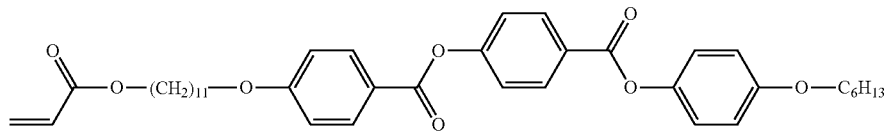
(A-4)
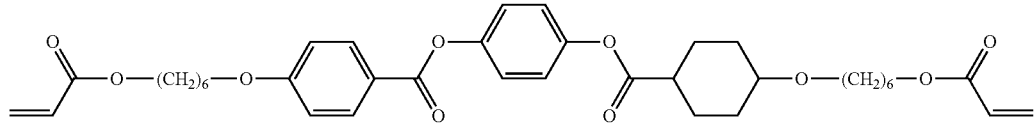
(A-5)
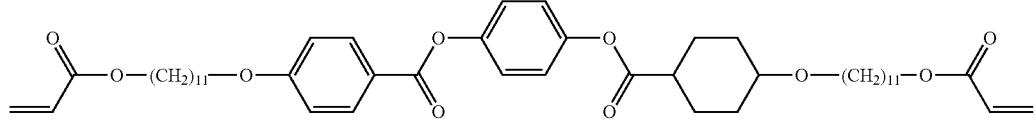
(A-6)
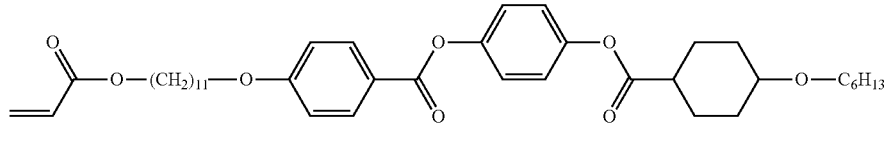
(A-7)
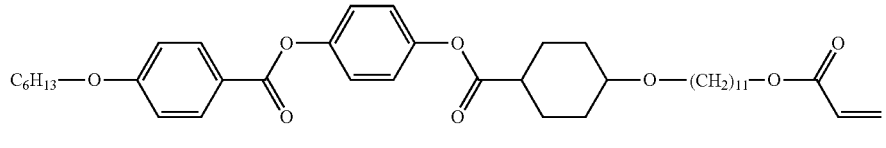
(A-8)
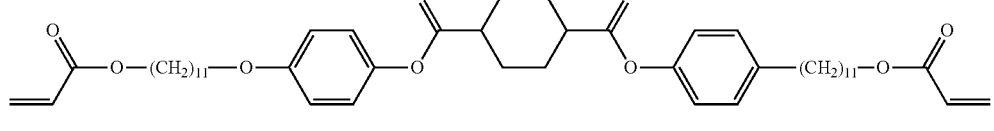
(A-9)
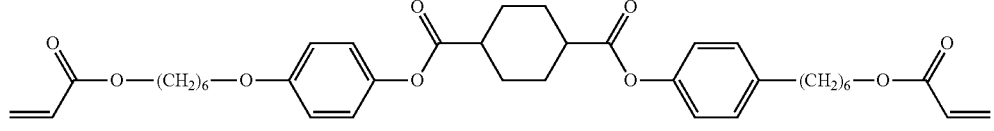
(A-10)
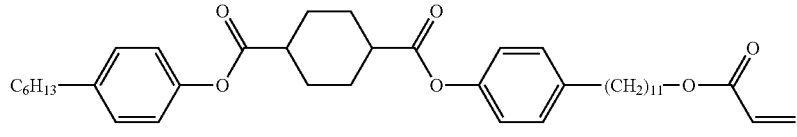
(A-11)
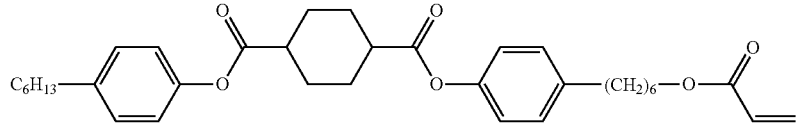
(A-12)
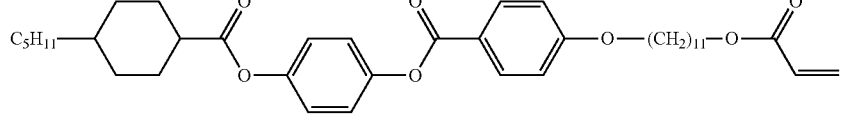
(A-13)

-continued

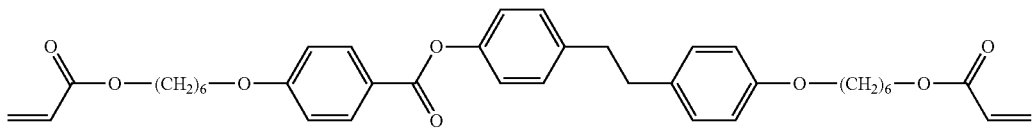
(A-14)

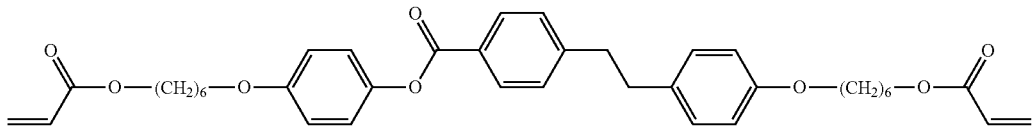
(A-15)

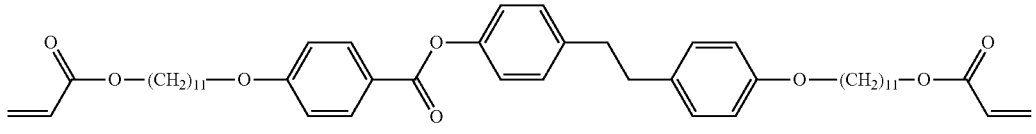
(A-16)

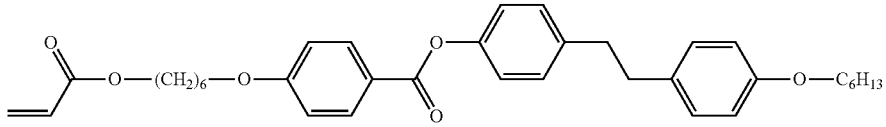
(A-17)

Among these compounds, polymerizable liquid crystal compound (A) is preferably at least one selected from the group consisting of compounds represented by any of formulas (A-2), (A-3), (A-4), (A-5), (A-6), (A-7), (A-8), (A-13), (A-14), (A-15), (A-16), and (A-17). Polymerizable liquid crystal compounds (A) may be used singly or in combination of two or more kinds thereof.

Polymerizable liquid crystal compound (A) can be produced, for example, by a method described in a known document such as Lub et al. Recl. Trav. Chim. Pays-Bas, 115, 321-328 (1996) or JP-B2-4719156.

Liquid Crystalline Polymer Compound

The liquid crystalline polymer compound may be a compound obtained by polymerizing the polymerizable liquid crystal compound (hereinafter, also referred to as a polymer of the polymerizable liquid crystal compound), or may be another liquid crystalline polymer compound, but is preferably a polymer of the polymerizable liquid crystal compound.

As the polymer of the polymerizable liquid crystal compound, two or more kinds of the polymerizable liquid crystal compounds may be used as raw material monomers. In addition, the polymer of the polymerizable liquid crystal compound may contain another monomer other than the polymerizable liquid crystal compound as a raw material monomer.

The content ratio of the polymerizable liquid crystal compound in the polymer of the polymerizable liquid crystal compound is usually 1 mol % or more and 100 mol % or less based on the total amount of constituent units derived from the polymerizable liquid crystal compound constituting the polymer of the polymerizable liquid crystal compound, and is preferably 30 mol % or more and 100 mol % or less, more preferably 50 mol % or more and 100 mol % or less, and still more preferably 80 mol % or more and 100 mol % or less from a viewpoint of enhancing the orientation of the polymer of the polymerizable liquid crystal compound.

Examples of the other liquid crystalline polymer compound include a polymer compound having a liquid crystalline group. Examples of the polymer compound serving as a mother skeleton include: a polyolefin such as polyethylene or polypropylene; a cyclic olefin resin such as a norbornene polymer; polyalkylene ether and polyvinyl alcohol; a polymethacrylate; and a polyacrylate. These polymer compounds each have a liquid crystalline group. Among these compounds, a polymethacrylate and a polyacrylate each having a liquid crystalline group are preferable.

The other liquid crystalline polymer compound may contain two or more kinds of liquid crystalline groups. The liquid crystalline group may be contained in a main chain of the polymer compound serving as the mother skeleton, may be contained in a side chain of the polymer compound serving as the mother skeleton, or may be contained in both the main chain and the side chain of the polymer compound serving as the mother skeleton. Examples of the liquid crystalline group include a group formed by removing one hydrogen atom from a compound having at least two hydrocarbon six-membered ring structures, and a group formed by removing two hydrogen atoms from the compound.

The content ratio of the liquid crystalline group in the other liquid crystalline polymer compound is usually 1 mol % or more and 100 mol % or less based on the total amount of constituent units constituting the polymer compound serving as the mother skeleton of the other liquid crystalline polymer compound, and preferably 30 mol % or more and 100 mol % or less, more preferably 50 mol % or more and 100 mol % or less, and still more preferably 80 mol % or more and 100 mol % or less from a viewpoint of enhancing the orientation of the other liquid crystalline polymer compound.

When two or more kinds of polymerizable liquid crystal compounds are used in combination in the composition, at least one of the polymerizable liquid crystal compounds is preferably polymerizable liquid crystal compound (A), and two or more kinds of the polymerizable liquid crystal compounds are each more preferably polymerizable liquid crystal compound (A). By using two or more kinds of polymerizable liquid crystal compounds in combination, the liquid crystal phase may be temporarily retained even at a temperature equal to or lower than a liquid crystal-crystal phase transition temperature. The total content of polymerizable liquid crystal compound (A) contained in the composition is preferably 40% by mass or more, and more preferably 60% by mass or more based on the total mass of all the polymerizable liquid crystal compounds in the composition, and all the polymerizable liquid crystal compounds may be each polymerizable liquid crystal compound (A). When the content of polymerizable liquid crystal compound (A) is within the above range, the polymerizable liquid crystal compounds are likely to be aligned with a high degree of orientation order, and the compound represented by formula (1A) is orientated along the polymerizable liquid crystal compounds, whereby a polarizing film having excellent polarizing performance can be obtained.

The total content ratio of a polymerizable liquid crystal compound and a liquid crystalline polymer compound in the composition is, for example, 50 parts by mass or more, preferably 70 parts by mass or more and 99.9 parts by mass or less, more preferably 70 parts by mass or more and 99.5 parts by mass or less, still more preferably 80 parts by mass or more and 99 parts by mass or less, particularly preferably 80 parts by mass or more and 94 parts by mass or less, and still more preferably 80 parts by mass or more and 90 parts by mass or less based on 100 parts by mass of the solid matter of the composition from a viewpoint of enhancing the orientation of the polymerizable liquid crystal compound and the liquid crystalline polymer compound.

The content of the azo compound (1A) in the composition is usually 0.1 parts by mass or more and 50 parts by mass or less, preferably 0.1 parts by mass or more and 20 parts by mass or less, more preferably 0.1 parts by mass or more and 10 parts by mass or less, and still more preferably 0.1 parts by mass or more and 5 parts by mass or less based on 100 parts by mass of the total amount of the polymerizable liquid crystal compound and the liquid crystalline polymer compound. When the content of the azo compound (1A) is 50 parts by mass or less based on the total amount of a polymerizable liquid crystal compound and a liquid crystalline polymer compound, there is a tendency that it is possible to obtain a polarizing film having a small orientation disorder of the polymerizable liquid crystal compound, the liquid crystalline polymer compound, and the azo compound (1A) and having a high degree of orientation order.

Polymer Compound

The composition may further contain a polymer compound in addition to the azo compound (1A), a polymerizable liquid crystal compound, and a liquid crystalline polymer compound. When the composition contains the polymer compound, the azo compound (1A) may be easily dispersed in the composition. The polymer compound that can be contained in the composition is not particularly limited as long as the polymer compound can easily disperse the azo compound (1A). An acrylic polymer such as polymethyl methacrylate (PMMA) is preferable from a viewpoint of easily dispersing the azo compound (1A) uniformly. In addition, the polymer compound may be a polymer compound obtained by polymerizing the above-described polymerizable liquid crystal compound. The polymer compound has a weight average molecular weight of, for example, 10,000 or more and 200,000 or less, preferably 20,000 or more and 150,000 or less in terms of polystyrene.

When the composition contains a polymer compound, the content of the polymer compound can be appropriately selected depending on a purpose and the like. The content of the polymer compound is preferably 10 parts by mass or less, more preferably 5.0 parts by mass or less, and still more preferably 3.0 parts by mass or less based on 100 parts by mass of the solid matter of the composition.

The composition preferably further contains a liquid medium such as a solvent and a polymerization initiator, and may further contain a photosensitizer, a polymerization inhibitor, a leveling agent, and the like as necessary.

Solvent

The solvent is preferably a solvent capable of completely dissolving the azo compound (1A), a polymerizable liquid crystal compound, a liquid crystalline polymer compound, and a polymer compound. In addition, the solvent is preferably inert to a polymerization reaction of the polymerizable liquid crystal compound.

Examples of the solvent include an alcohol solvent, an ester solvent, a ketone solvent, an aliphatic hydrocarbon solvent, an aromatic hydrocarbon solvent, a nitrile solvent, an ether solvent, and a chlorine-containing solvent. These solvents may be used singly or in combination of two or more kinds thereof.

When the composition contains the solvent, the content ratio of the solvent is preferably 50% by mass or more and 98% by mass or less based on the total amount of the composition. In other words, the content ratio of the solid matter in the composition is preferably 2% by mass or more and 50% by mass or less. When the solid matter is 50% by mass or less, the viscosity of the composition decreases, a film obtained from the composition, for example, the thickness of the film is substantially uniform, and unevenness tends to be hardly generated in the film. The content ratio of the solid matter can be determined in consideration of the thickness of a film to be produced.

Polymerization Initiator

The polymerization initiator is a compound capable of initiating a polymerization reaction of a polymerizable liquid crystal compound. The polymerization initiator is preferably a photopolymerization initiator in that the photopolymerization initiator can initiate a polymerization reaction under lower temperature conditions. Specific examples of the photopolymerization initiator include a photopolymerization initiator capable of generating an active radical or an acid by action of light. Among these photopolymerization initiators, a photopolymerization initiator that generates a radical by action of light is preferable.

Examples of the polymerization initiator include a benzoin compound, a benzophenone compound, an alkylphenone compound, an acylphosphine oxide compound, a triazine compound, an iodonium salt, and a sulfonium salt. The polymerization initiator can be appropriately selected from known polymerization initiators depending on a purpose and the like. In addition, the polymerization initiator may be used singly or in combination of two or more kinds thereof.

When the composition contains a polymerization initiator, the content of the polymerization initiator only needs to be appropriately determined depending on the kind and amount of a polymerizable liquid crystal compound contained in the composition. The content of the polymerization initiator is, for example, 0.001 parts by mass or more, 0.01 parts by mass or more, 0.1 parts by mass or more, or 0.5 parts by mass or more, and is, for example, 30% by mass or less, 10% by mass or less, or 8% by mass or less based on 100 parts by mass of the polymerizable liquid crystal compound. In addition, the content of the polymerization initiator is preferably 0.001 parts by mass or more and 30 parts by mass or less, more preferably 0.01 parts by mass or more and 10 parts by mass or less, and still more preferably 0.1 parts by mass or more and 8 parts by mass or less based on 100 parts by mass of the polymerizable liquid crystal compound. When the content of the polymerizable initiator is within the above range, the polymerizable liquid crystal compound can be polymerized without causing orientation disorder for the polymerizable liquid crystal compound.

Photosensitizer

When the composition contains a photopolymerization initiator, the composition may preferably contain at least one photosensitizer. When the composition contains a photopolymerization initiator and a photosensitizer, a polymerization reaction of a polymerizable liquid crystal compound tends to be further promoted. Examples of the photosensitizer include a xanthone compound such as xanthone or thioxanthone; an anthracene compound such as anthracene or an anthracene having an alkoxy group as a substituent; phenothiazine; and rubrene. The photosensitizer can be used singly or in combination of two or more kinds thereof.

When the composition contains a photosensitizer, the content of the photosensitizer in the composition only needs to be appropriately determined depending on the kinds and amounts of a photopolymerization initiator and a polymerizable liquid crystal compound. The content of the photosensitizer in the composition is preferably 0.1 parts by mass or more and 30 parts by mass or less, more preferably 0.5 parts by mass or more and 10 parts by mass or less, and still more preferably 0.5 parts by mass or more and 8 parts by mass or less based on 100 parts by mass of the polymerizable liquid crystal compound.

Polymerization Inhibitor

The composition may contain at least one polymerization inhibitor. Examples of the polymerization inhibitor include a radical scavenger such as hydroquinone, an alkoxy group-containing hydroquinone, an alkoxy group-containing catechol (for example, butylcatechol), pyrogallol, or a 2,2,6,6-tetramethyl-1-piperidinyloxy radical; a thiophenol; and a β-Naphthylamine and a β-naphthol. When the composition contains a polymerization inhibitor, the degree of progress of a polymerization reaction of a polymerizable liquid crystal compound can be controlled.

When the composition contains a polymerization inhibitor, the content of the polymerization inhibitor in the composition is preferably 0.1 parts by mass or more and 30 parts by mass or less, more preferably 0.5 parts by mass or more and 10 parts by mass or less, and still more preferably 0.5 parts by mass or more and 8 parts by mass or less based on 100 parts by mass of the polymerizable liquid crystal compound.

Leveling Agent

The composition may contain at least one leveling agent. The leveling agent has a function of adjusting fluidity of the composition and making a coating film obtained by applying the composition flatter, and specific examples of the leveling agent include a surfactant. The leveling agent is preferably at least one selected from the group consisting of a leveling agent containing a polyacrylate compound as a main component and a leveling agent containing a fluorine atom-containing compound as a main component. The leveling agent can be used singly or in combination of two or more kinds thereof.

When the composition contains a leveling agent, the content of the leveling agent is preferably 0.05 parts by mass or more and 5 parts by mass or less, and more preferably 0.05 parts by mass or more and 3 parts by mass or less based on 100 parts by mass of the total amount of a polymerizable liquid crystal compound and a liquid crystalline polymer compound. When the content of the leveling agent is within the above range, the polymerizable liquid crystal compound and the liquid crystalline polymer compound are easily horizontally orientated, unevenness tends to be hardly generated, and a smoother film, for example, a polarizing film tends to be obtained.

When the content of the leveling agent is within the above range, the polymerizable liquid crystal compound and the liquid crystalline polymer compound are easily horizontally orientated, and an obtained film tends to be smoother. When the content of the leveling agent based on the polymerizable liquid crystal compound and the liquid crystalline polymer compound exceeds the above range, unevenness tends to be easily generated in an obtained film.

Antioxidant

The composition may contain an antioxidant. The antioxidant is not particularly limited as long as the composition can exhibit the effect of the present invention, and a known antioxidant can be used. The antioxidant is preferably a so-called primary antioxidant that traps radicals and has an action of preventing automatic oxidation from a viewpoint of having a high effect of suppressing photodegradation of the azo compound (1A). Therefore, the antioxidant contained in the composition is more preferably at least one selected from the group consisting of a phenolic compound, an alicyclic alcohol-based compound, and an amine-based compound. The antioxidant may be used singly or in combination of two or more kinds thereof.

The content of the antioxidant in the composition is preferably 0.1 parts by mass or more and 15 parts by mass or less, more preferably 0.3 parts by mass or more, still more preferably 0.5 parts by mass or more, more preferably 12 parts by mass or less, and still more preferably 10 parts by mass or less based on 100 parts by mass of the composition. When the content of the antioxidant is the above lower limit value or more, photodegradation of the azo compound (1A) can be more effectively suppressed. In addition, when the content of the antioxidant is the above upper limit value or less, orientation disorder of the polymerizable liquid crystal compound is less likely to occur, and a higher suppressing effect on photodegradation of the azo compound (1A) can be expected.

The composition may contain another additive other than those described above. Examples of the other additive include a release agent, a stabilizer, a colorant such as a bluing agent, a flame retardant, and a lubricant. When the composition contains the other additive, the content of the other additive is preferably more than 0% and 20% by mass or less, and more preferably more than 0% and 10% by mass or less based on the solid matter of the composition.

The composition can be produced by a conventionally known method for preparing the composition. For example, the composition can be prepared by mixing and stirring the azo compound (1A), a liquid crystalline compound, and as necessary, an additive such as an antioxidant or a leveling agent.

<Film>

A film according to the present embodiment may be a film containing the azo compound (1A) as a forming material, or may be a film obtained using a composition containing the azo compound (1A) and a liquid crystalline compound as a forming material. The film formed from the composition may be formed by applying the composition to a substrate to form the film. In addition, when the composition contains a polymerizable liquid crystal compound, a film containing a cured product obtained by polymerizing the polymerizable liquid crystal compound may be formed by applying the composition to a substrate, forming a film, and then polymerizing and curing the polymerizable liquid crystal compound.

The composition can form a film having a high degree of orientation order, for example, a polarizing film. Therefore, the film according to the present embodiment is a polarizing film formed from a composition containing the azo compound (1A) and a liquid crystalline compound, and includes a polarizing film having a high degree of orientation order.

Here, in the polarizing film having a high degree of orientation order, a Bragg peak derived from a higher-order structure such as a hexatic phase or a crystal phase is obtained in X-ray diffractometry. Therefore, the polarizing film formed from the composition is preferably orientated such that the polymerizable liquid crystal compound or the liquid crystalline polymer compound exhibits a Bragg peak in X-ray diffractometry, and more preferably "horizontally orientated" such that the molecules of the polymerizable liquid crystal compound or the liquid crystalline polymer compound are orientated in a light absorbing direction. The high degree of orientation order indicating a Bragg peak can be achieved by controlling the kind of a polymerizable liquid crystal compound or a liquid crystalline polymer compound to be used, the amount of the azo compound (1A), and the like.

The azo compound (1A) and the liquid crystalline compound constituting the composition used for forming the film are as described above.

The film can be produced, for example, by a method including the following steps.

Step A: forming a coating film of a composition containing the azo compound (1A), a liquid crystalline compound, and a solvent;

Step B: removing at least a part of the solvent from the coating film;

Step C: raising the temperature to a temperature equal to or higher than a temperature at which the liquid crystalline compound undergoes phase transition to a liquid phase, and then lowering the temperature to cause the liquid crystalline compound to undergo phase transition to a smectic phase (smectic liquid crystal state); and Step D: as necessary, polymerizing the polymerizable liquid crystal compound while maintaining the smectic phase (smectic liquid crystal state).

The coating film of the composition can be formed, for example, by applying the composition onto a substrate, an orientation film described later, or the like. Alternatively, the composition may be directly applied onto a phase difference film constituting a polarizing plate or another layer.

The substrate is usually a transparent substrate. Note that when the substrate is not disposed on a display surface of a display element, for example, when a laminate obtained by removing the substrate from the film is disposed on the display surface of the display element, the substrate does not have to be transparent. The transparent substrate means a substrate having transparency capable of transmitting light, particularly visible light, and the transparency refers to a characteristic that transmittance to light in a wavelength range of 380 nm or more and 780 nm or less is 80% or more. Specific examples of the transparent substrate include a translucent resin substrate.

Examples of a resin constituting the translucent resin substrate include: a polyolefin; a cyclic olefin-based resin; polyvinyl alcohol; polyethylene terephthalate; polymethacrylate; polyacrylate; a cellulose ester; polyethylene naphthalate; polycarbonate; polysulfone; polyethersulfone; polyether ketone; polyphenylene sulfide; and polyphenylene oxide. Polyethylene terephthalate, polymethacrylate, a cellulose ester, a cyclic olefin-based resin, or polycarbonate is preferable from a viewpoint of easy availability and transparency.

Characteristics required for the substrate vary depending on a configuration of a film. However, usually, a substrate having a phase difference as small as possible is preferable. Examples of the substrate having a phase difference as small as possible include a cellulose ester film having no phase difference, such as zero tack (Konica Minolta Opto Co., Ltd.) or Z tack (Fujifilm Corporation). In addition, an unstretched cyclic olefin-based resin substrate is also preferable. A surface of the substrate on which the film is not laminated may be subjected to a hard coat treatment, an antireflection treatment, an antistatic treatment, or the like.

The thickness of the substrate is usually 5 μm or more and 300 μm or less, preferably 20 μm or more and 200 μm or less, and more preferably 20 μm or more and 100 μm or less. When the thickness is equal to or more than the lower limit value, reduction in strength is suppressed, and workability tends to be favorable.

Examples of a method for applying the composition to the substrate or the like include known methods including: an application method such as a spin coating method, an extrusion method, a gravure coating method, a die coating method, a bar coating method, or an applicator method; and a printing method such as a flexography method.

Subsequently, at least a part of the solvent contained in the coating film obtained from the composition is removed by drying or the like to form a dry coating film. In addition, when the polymerizable liquid crystal compound is contained in the coating film, drying is performed under a condition that the polymerizable liquid crystal compound is not polymerized to form a dry coating film. Examples of the method for drying the coating film include a natural drying method, a forced-air drying method, a heating drying method, and a reduced-pressure drying method.

Furthermore, in order to cause the liquid crystalline compound to undergo phase transition to a liquid phase, the temperature is raised to a temperature equal to or higher than a temperature at which the liquid crystalline compound undergoes phase transition to the liquid phase, and then the temperature is lowered to cause the liquid crystalline compound to undergo phase transition to a smectic phase (smectic liquid crystal state). Such phase transition may be performed after removal of the solvent in the coating film, or may be performed simultaneously with removal of the solvent.

When the composition contains a polymerizable liquid crystal compound, by polymerizing the polymerizable liquid crystal compound while maintaining the smectic liquid crystal state of the polymerizable liquid crystal compound, a film including a cured product of the polymerizable liquid crystal compound is formed. As a polymerization method, a photopolymerization method is preferable. In photopolymerization, light with which a dry coating film is irradiated is appropriately selected depending on the kind of a photopolymerization initiator contained in the dry coating film, and the kind and the amount of the polymerizable liquid crystal compound (particularly, the kind of a polymerizable group of the polymerizable liquid crystal compound). Specific examples of the light include one or more kinds of light selected from the group consisting of visible light, ultraviolet light, infrared light, an X-ray, an α-ray, a β-ray, and a γ-ray, and an active electron beam. Among these kinds of light, ultraviolet light is preferable in that it is easy to control progress of a polymerization reaction and those widely used in the art can be used as a photopolymerization device. It is preferable to select the kinds and the like of the polymerizable liquid crystal compound and the photopolymerization initiator contained in the composition such that photopolymerization with ultraviolet light is possible. In addition, a polymerization temperature can also be controlled by irradiating the dry coating film with light while cooling the dry coating film by an appropriate cooling means during polymerization. By adopting such a cooling means, if the polymerizable liquid crystal compound is polymerized at a lower temperature, a film can be appropriately formed even if a substrate having relatively low heat resistance is used. During photopolymerization, a patterned film can also be obtained, for example, by performing masking or development.

Examples of a light source of the active energy ray include a low pressure mercury lamp, a medium pressure mercury lamp, a high pressure mercury lamp, an ultra-high pressure mercury lamp, a xenon lamp, a halogen lamp, a carbon arc lamp, a tungsten lamp, a gallium lamp, an excimer laser, an LED light source that emits light in a wavelength range of 380 nm or more and 440 nm or less, a chemical lamp, a black light lamp, a microwave-excited mercury lamp, and a metal halide lamp.

An ultraviolet irradiation intensity may be usually 10 $mW/cm^2$ or more and 3,000 $mW/cm^2$ or less. The ultraviolet irradiation intensity is preferably an intensity in a wavelength region effective for activating a photopolymerization initiator. Light irradiation time may be usually 0.1 seconds or more and 10 minutes or less, is preferably 0.1 seconds or more and 5 minutes or less, more preferably 0.1 seconds or more and 3 minutes or less, and still more preferably 0.1 seconds or more and 1 minute or less. When irradiation is performed once or a plurality of times with such an ultraviolet irradiation intensity, an integrated light amount thereof is preferably 10 $mJ/cm^2$ or more and 3,000 $mJ/cm^2$ or less.

By performing photopolymerization, the polymerizable liquid crystal compound is polymerized while maintaining a smectic phase liquid crystal state, preferably a high-order smectic phase liquid crystal state to form a film. The film obtained by polymerizing the polymerizable liquid crystal compound while the polymerizable liquid crystal compound maintains a smectic phase liquid crystal state advantageously has higher polarizing performance than a conventional host-guest type polarizing film, that is, a film having a nematic phase liquid crystal state due to an action of a dichroic dye. Furthermore, the film obtained by polymerizing the polymerizable liquid crystal compound while the polymerizable liquid crystal compound maintains a smectic phase liquid crystal state advantageously has better strength than a film to which only a dichroic dye or a lyotropic liquid crystal is applied.

The thickness of the film can be appropriately selected depending on a display device to be applied or the like, and is preferably 0.5 µm or more and 10 µm or less, more preferably 1 µm or more and 5 µm or less, and still more preferably 1 µm or more and 3 µm or less.

When the film is used as a polarizing film, the film is preferably formed on an orientation film. The orientation film has an orientation controlling force for liquid crystal-orientating a polymerizable liquid crystal compound and a liquid crystalline polymer compound in a desired direction. The orientation film preferably has solvent resistance not to be dissolved by application or the like of a composition containing a liquid crystalline compound containing at least one of a polymerizable liquid crystal compound and a liquid crystalline polymer compound, and also has heat resistance in a heat treatment for removing a solvent or orientating a polymerizable liquid crystal compound. Examples of such an orientation film include an orientation film containing an orientational polymer, a photo-orientation film, and a groove orientation film having irregular patterns or a plurality of grooves on a surface thereof. A photo-orientation film is preferable from a viewpoint of the accuracy of an orientation angle and quality.

<Laminate>

A laminate according to the present embodiment may include a film containing the azo compound (1A) as a forming material, or may include a film containing a composition containing the azo compound (1A) and a liquid crystalline compound as a forming material. The laminate may include a substrate and a film disposed on the substrate and containing the azo compound (1A) as a forming material, or may include a substrate, an orientation film disposed on the substrate, and a film disposed on the orientation film and containing the azo compound (1A) as a forming material. The film containing the azo compound (1A) as a forming material may constitute a polarizing film. In addition, the substrate may be a phase difference film. The laminate can constitute, for example, a polarizing plate. The laminate can be produced, for example, by forming a film on a substrate according to the above-described method for producing a film.

The thickness of the laminate is preferably 10 µm or more and 300 µm or less, more preferably 20 µm or more and 200 µm or less, and still more preferably 25 µm or more and 100 µm or less from a viewpoint of flexibility and visibility of a display device.

When the laminate includes a phase difference film as a substrate, the thickness of the phase difference film can be appropriately selected depending on an applied display device.

<Display Device>

A display device of the present embodiment includes the laminate, and the laminate may be a polarizing plate. The display device can be obtained, for example, by bonding the laminate as a polarizing plate to a surface of the display device with an adhesive layer interposed therebetween. The display device is a device having a display element, and is a device including a light emitting element or a light emitting device as a light emitting source. Examples of the display device include a liquid crystal display device, an organic electroluminescence (EL) display device, an inorganic electroluminescence (EL) display device, an electron emission display device (for example, a field emission display device (FED) or a surface field emission display device (SED)), an electronic paper (display device using electronic ink, an electrophoresis element, and the like), a plasma display device, a projection-type display device (for example, a grating light valve (GLV) display device or a display device having a digital micromirror device (DMD)), and a piezoelectric ceramic display. The liquid crystal display device includes any of a transmissive liquid crystal display device, a semi-transmissive liquid crystal display device, a reflective liquid crystal display device, a direct view type liquid crystal display device, a projection type liquid crystal display device, and the like. These display devices may be display devices that display two-dimensional images or stereoscopic display devices that display three-dimensional images. In particular, as the display device, an organic EL display device and a touch panel display device are preferable, and in particular, an organic EL display device is preferable.

EXAMPLES

Hereinafter, the present invention will be specifically described with reference to Examples, but the present invention is not limited to these Examples.

Compound (1-1-a) and compound (1-3-a) were synthesized by a known diazo coupling method.

Synthesis Example 1: Synthesis of Compound (1-1)

Compound (1-1-a) (0.139 g, 0.299 mmol) and imidazole (0.061 g, 0.90 mmol) were dissolved in N,N-dimethylformamide (5.0 mL), and the resulting solution was cooled to 0° C. Thereafter, chlorotriethylsilane (0.095 g, 0.63 mmol) was added thereto, the temperature was returned to room temperature, and the mixture was stirred for five hours. Water was added to the reaction vessel, and the precipitated solid was separated by filtration and washed with methanol. The obtained solid was purified by silica gel column chromatography using chloroform as an eluent to obtain compound (1-1) (0.130 g, yield 75%).

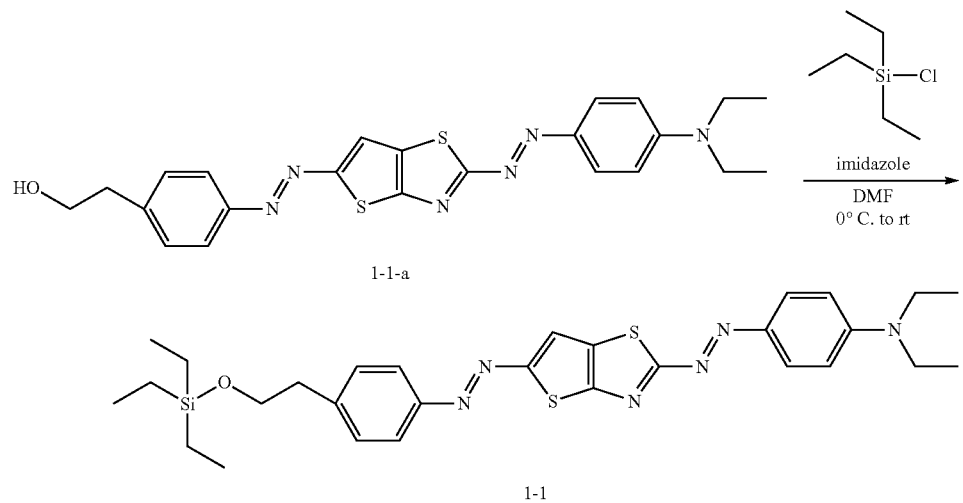

$^1$H-NMR (400 MHz, CDCl$_3$): δ (ppm)=7.95 (d, 2H), 7.91 (s, 1H), 7.80 (d, 2H), 7.33 (d, 2H), 6.75 (d, 2H), 3.85 (t, 2H), 3.52 (q, 4H), 2.91 (t, 2H), 1.28 (t, 6H), 0.93 (t, 9H), 0.57 (q, 6H)

UV visible light spectrum: λmax=593 nm (in chloroform)

Synthesis Example 2: Synthesis of Compound (1-2)

Compound (1-1-a) (0.139 g, 0.299 mmol) and imidazole (0.061 g, 0.90 mmol) were dissolved in N,N-dimethylformamide (5.0 mL), and the resulting solution was cooled to 0° C. Thereafter, chlorodimethyltexylsilane (0.112 g, 0.626 mmol) was added thereto, the temperature was returned to room temperature, and the mixture was stirred for five hours. Water was added to the reaction vessel, and the precipitated solid was separated by filtration and washed with methanol. The obtained solid was purified by silica gel column chromatography using chloroform as an eluent to obtain compound (1-2) (0.130 g, yield 75%).

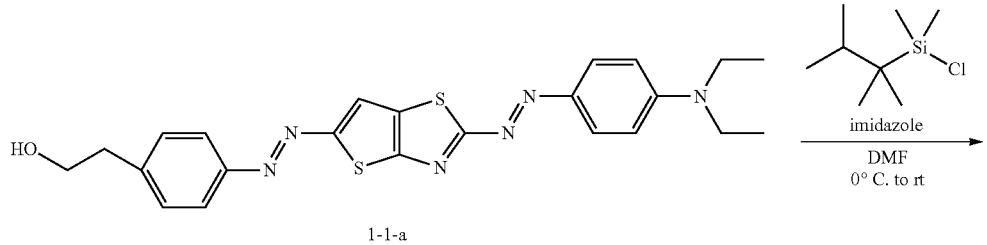

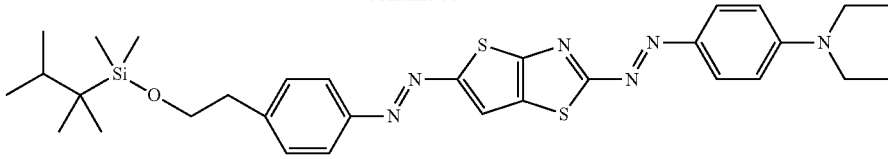

1-2

$^1$H-NMR (400 MHz, CDCl$_3$): δ (ppm)=7.95 (d, 2H), 7.91 (s, 1H), 7.80 (d, 2H), 7.33 (d, 2H), 6.75 (d, 2H), 3.84 (t, 2H), 3.52 (q, 4H), 2.88 (t, 2H), 1.63-1.58 (m, 1H), 1.28 (t, 6H), 0.86 (m, 6H), 0.82 (m, 6H), 0.03 (s, 6H)

UV visible light spectrum: λmax=592 nm (in chloroform)

Synthesis Example 3: Synthesis of Compound 1-3

Compound (1-3-a) (1.127 g, 2.501 mmol) and imidazole (0.256 g, 3.76 mmol) were dissolved in tetrahydrofuran (25.0 mL), and the resulting solution was cooled to 0° C. Thereafter, chlorodimethyltexylsilane (0.492 g, 2.77 mmol) was added thereto, the temperature was returned to room temperature, and the mixture was stirred for five hours. Water was added to the reaction vessel, and the precipitated solid was separated by filtration and washed with methanol. The obtained solid was purified by silica gel column chromatography using chloroform as an eluent to obtain compound (1-3) (0.690 g, yield 47%).

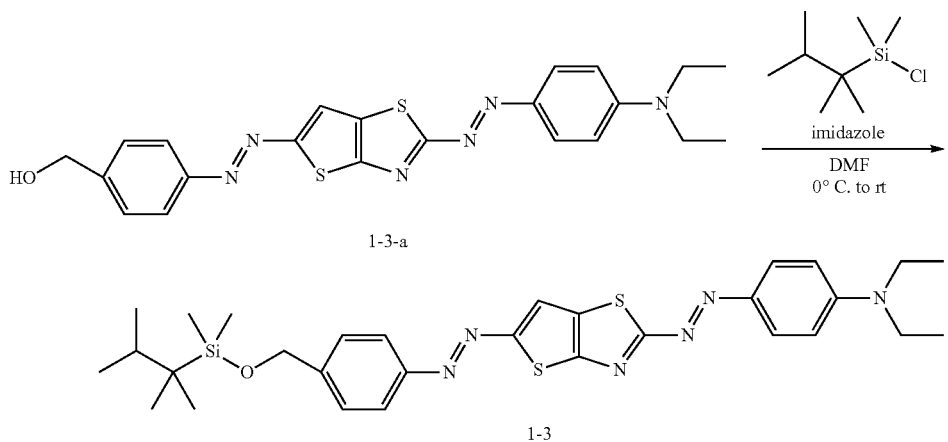

$^1$H-NMR (400 MHz, CDCl$_3$): δ (ppm)=7.95 (d, 2H), 7.91 (s, 1H), 7.80 (d, 2H), 7.33 (d, 2H), 6.75 (d, 2H), 4.80 (s, 2H), 3.52 (q, 4H), 1.69 (sep, 1H), 1.28 (t, 6H), 0.93 (m, 6H), 0.89 (m, 6H), 0.16 (s, 6H)

UV visible light spectrum: λmax=593 nm (in chloroform)

Synthesis Example 4: Synthesis of Compound (1-93)

Compound (1-1-a) (0.500 g, 1.05 mmol) and imidazole (0.219 g, 3.20 mmol) were dissolved in N,N-dimethylformamide (10.5 mL), and the resulting solution was cooled to 0° C. Thereafter, tert-butyldiphenylchlorosilane (0.596 g, 2.10 mmol) was added thereto, the temperature was returned to room temperature, and the mixture was stirred for five hours. Water was added to the reaction vessel, and the precipitated solid was separated by filtration and washed with methanol. The obtained solid was purified by silica gel column chromatography using chloroform as an eluent to obtain compound (1-93) (0.614 g, yield 82%).

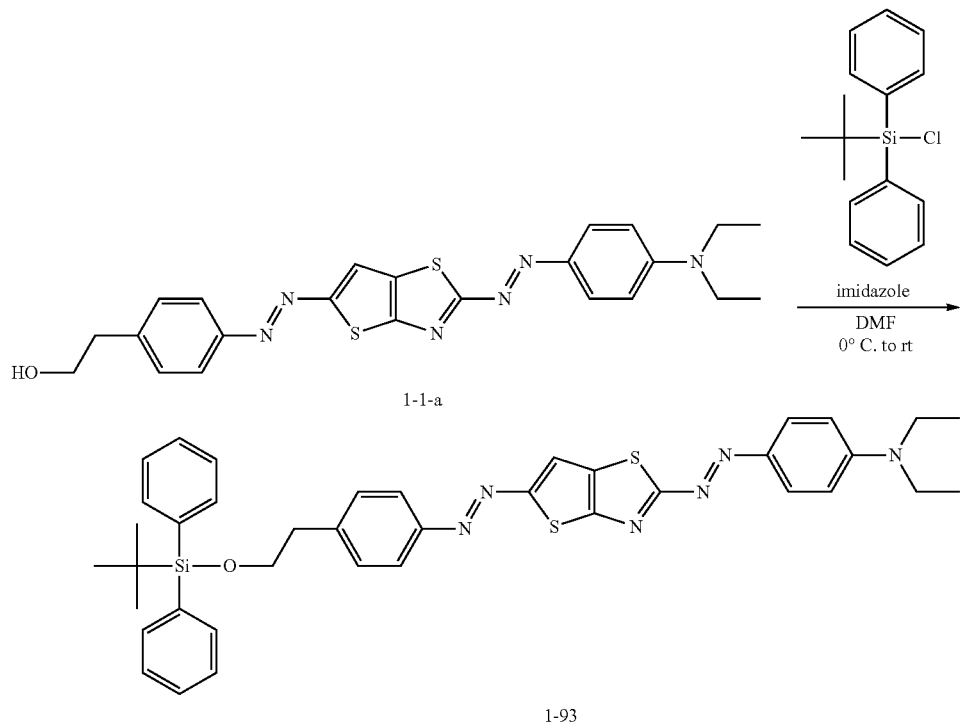

$^1$H-NMR (400 MHz, CDCl$_3$): δ (ppm)=7.93 (d, 2H), 7.90 (s, 1H), 7.77 (d, 2H), 7.57 (dd, 4H), 7.46-7.32 (m, 6H), 7.27 (d, 2H), 6.74 (d, 2H), 3.88 (t, 2H), 3.51 (q, 4H), 2.90 (t, 2H), 1.27 (t, 6H), 1.01 (t, 9H), 0.57 (q, 6H)

UV visible light spectrum: λmax=592 nm (in chloroform)

Comparative Synthesis Example 1: Synthesis of Compound (2-1)

Compound 1-1-a (0.186 g, 0.400 mmol), N,N-diisopropylcarbodiimide (1.01 g, 8.00 mmol), 4-dimethylaminopyridine (0.012 g, 0.098 mmol), and 2-ethylhexanoic acid (0.149 g, 1.03 mmol) were mixed, and the resulting mixture was stirred at room temperature for 15 hours. A saturated sodium bicarbonate aqueous solution was added to the reaction vessel, and the precipitated solid was separated by filtration and washed with methanol. The obtained solid was purified by silica gel column chromatography using chloroform as an eluent to obtain compound (2-1) (0.049 g, yield 21%).

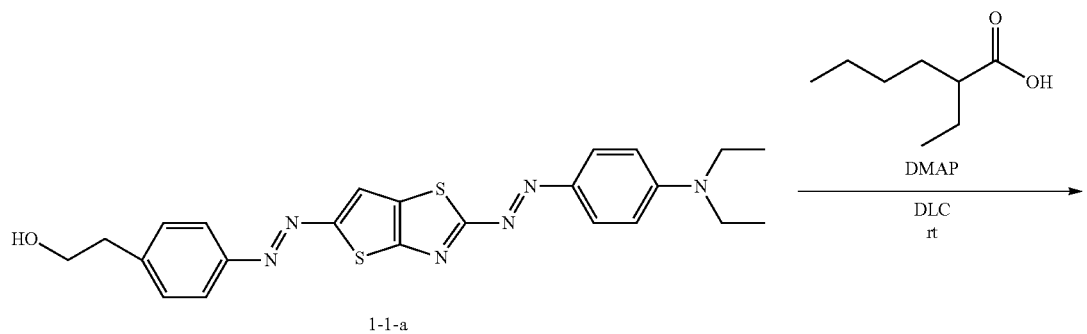

-continued

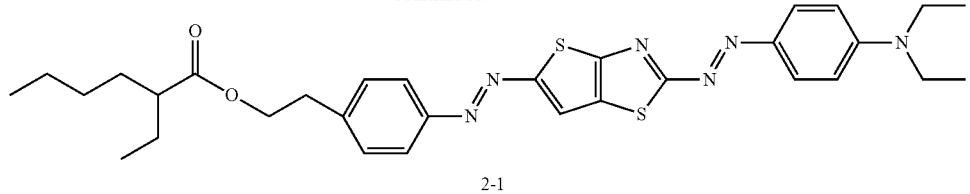

2-1

¹H-NMR (400 MHz, CDCl₃): δ (ppm)=7.95 (d, 2H), 7.92 (s, 1H), 7.82 (d, 2H), 7.36 (d, 2H), 6.75 (d, 2H), 4.36 (t, 2H), 3.52 (q, 4H), 3.03 (t, 2H), 2.19 (quin, 1H), 1.60 (m, 2H) 1.56 (m, 2H), 1.54 (m, 2H) 1.50 (m, 2H), 1.28 (t, 6H), 0.84 (t, 6H)

UV visible light spectrum: λmax=594 nm (in chloroform)

The following compounds (2-2) and (2-3) were synthesized by a known diazo coupling method.

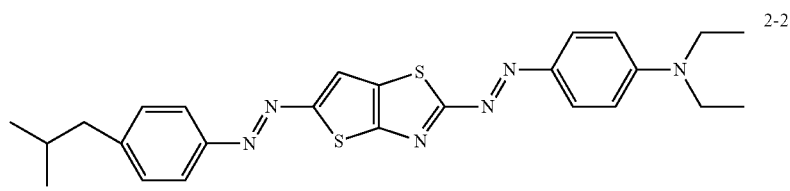

2-2

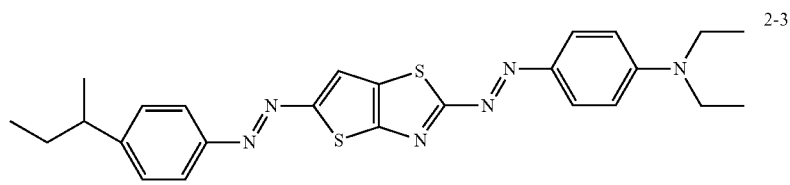

2-3

Example 1: Preparation of Composition E1 Containing Compound (1-1)

The following components were mixed and stirred at 90° C. for one hour to obtain composition E1.

Compound (1-1) 4.0 parts by mass
Polymerizable liquid crystal compound (A-6) 75 parts by mass
Polymerizable liquid crystal compound (A-8) 25 parts by mass
Polymerizable non-liquid crystal compound 5 parts by mass
Dipentaerythritol hexaacrylate (manufactured by Daicel Cytec Co., Ltd.)
Polymerization initiator 6 parts by mass
2-Dimethylamino-2-benzyl-1-(4-morpholinophenyl) butan-1-one (IRGACURE 369; manufactured by BASF Japan Ltd.)
Leveling agent 1.2 parts by mass
Polyacrylate compound (BYK-361N; manufactured by BYK-Chemie)
Solvent: Toluene 250 parts by mass The structure of the polymerizable liquid crystal compound is as follows. Note that the polymerizable liquid crystal compounds (A-6) and A-8) were synthesized by a method described in Lub et al. Recl. Trav. Chim. Pays-Bas, 115, 321-328 (1996).

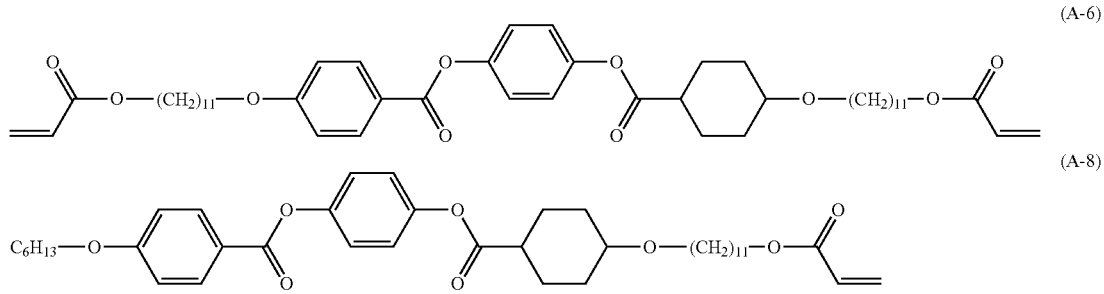

Using the obtained composition E1, a polarizing film was formed as follows.

1. Formation of Orientation Film

A glass substrate was used as a substrate. A 2% by mass polyvinyl alcohol (polyvinyl alcohol 1000, completely saponified type, manufactured by FUJIFILM Wako Pure Chemical Corporation) aqueous solution (orientation film polymer composition) was applied onto the glass substrate by a spin coating method, and dried to form a film having a thickness of 100 nm. Subsequently, a surface of the obtained film was rubbed to form an orientation layer. The rubbing treatment was performed by using a semi-automatic rubbing device (trade name: LQ-008 type, manufactured by Joyo Engineering Co., Ltd.) and a cloth (trade name: YA-20-RW, manufactured by Yoshikawa Chemical Co., Ltd.) under conditions of a pushing amount of 0.15 mm, a rotation speed of 500 rpm, and 16.7 mm/s. By the rubbing treatment, a laminate (1) in which an orientation film was formed on the glass substrate was obtained.

2. Formation of Polarizing Film

The obtained composition E1 was applied onto the orientation film of the laminate (1) by a spin coating method, heated and dried on a hot plate at 120° C. for one minute, and then rapidly cooled to room temperature to form a dried film on the orientation layer. Subsequently, using a UV irradiation device (SPOT CURE SP-7; manufactured by USHIO Inc.), the dried film was irradiated with an ultraviolet ray at an exposure amount of 2000 mJ/cm2 (313 nm standard) to polymerize a polymerizable liquid crystal compound contained in the dried film to form a polarizing film from the dried film, thus obtaining a laminate (2). The thickness of the polarizing film at this time was measured by a laser microscope (OLS 3000 manufactured by Olympus Corporation) and found to be 1.8 μm.

Example 2

Composition E2 was obtained in a similar manner to Example 1 except that compound (1-2) was used instead of compound (1-1). A laminate (2) on which a polarizing film was formed was obtained in a similar manner to Example 1 except that the obtained composition E2 was used.

Example 3

Composition E3 was obtained in a similar manner to Example 1 except that compound (1-3) was used instead of compound (1-1). A laminate (2) on which a polarizing film was formed was obtained in a similar manner to Example 1 except that the obtained composition E3 was used.

Example 4

Composition E4 was obtained in a similar manner to Example 1 except that compound (1-93) was used instead of compound (1-1). A laminate (2) on which a polarizing film was formed was obtained in a similar manner to Example 1 except that the obtained composition E4 was used.

Comparative Example 1

Composition C1 was obtained in a similar manner to Example 1 except that compound (2-1) was used instead of compound (1-1). A laminate (2) on which a polarizing film was formed was obtained in a similar manner to Example 1 except that the obtained composition C1 was used.

Comparative Example 2

Composition C2 was obtained in a similar manner to Example 1 except that compound (2-2) was used instead of compound (1-1). A laminate (2) on which a polarizing film was formed was obtained in a similar manner to Example 1 except that the obtained composition C2 was used.

Comparative Example 3

Composition C3 was obtained in a similar manner to Example 1 except that compound (2-3) was used instead of compound (1-1). A laminate (2) on which a polarizing film was formed was obtained in a similar manner to Example 1 except that the obtained composition C3 was used.

<Evaluation>

Absorbance Retention Ratio

Storage stability of each of the compositions obtained above as a composition was evaluated as follows. Immediately after the preparation of the compositions (within 10 minutes), each of the compositions was diluted with chloroform, and an initial absorbance was measured at a maximum absorption wavelength of an absorption spectrum. The diluted solution was stored at room temperature (25° C.), and the absorbance at the maximum absorption wavelength was measured again after one day and after five days from the preparation. The absorbance that had been measured again was divided by the initial absorbance to calculate absorbance retention ratios (%) after one day and after five days, respectively, and evaluated according to the following evaluation criteria. Results thereof are indicated in Table 1.

Evaluation Criteria

A: The absorbance retention ratio was 70% or more and 100% or less.

B: The absorbance retention ratio was 45% or more and less than 70%.

C: The absorbance retention ratio was less than 45%.

Evaluation of Polarizing Film

For an appearance of each of the polarizing films obtained above, presence or absence of orientation defects due to crystal precipitation was observed visually and with a microscope, and evaluated according to the following evaluation criteria. Results thereof are indicated in Table 1.

Evaluation Criteria

A: Orientation defects were not confirmed, and good orientation was maintained.

B: Orientation defects were slightly confirmed, but the film was resistant to use as a polarizing film.

C: Orientation defects were confirmed, and the film was not suitable for use as a polarizing film.

A dichroic ratio of the laminate (2) obtained above was measured as follows. Absorbance (A1) of the polarizing film of the laminate (2) at a maximum absorption wavelength (λmax) in a transmission axis direction and absorbance (A2) of the polarizing film of the laminate (2) at a maximum absorption wavelength (λmax) in an absorption axis direction were measured by a double beam method using a device in which a folder including the laminate (2) was set in a spectrophotometer (UV-3150 manufactured by Shimadzu Corporation). In the folder, a mesh for cutting the amount of light by 50% was disposed on a reference side. From the measured values of absorbance (A1) in the transmission axis direction and absorbance (A2) in the absorption axis direction, a ratio (A2/A1) was calculated and taken as a dichroic ratio (DR). Results thereof are indicated in Table 1. Note that, in the table, "–" indicates unevaluated.

TABLE 1

|  | Absorbance retention ratio | | Appearance of | | |
| --- | --- | --- | --- | --- | --- |
|  | After one day | After five days | polarizing film | Dichroic ratio | λmax (nm) |
| Example 1 | A | A | A | 76 | 650 |
| Example 2 | A | A | A | 70 | 649 |
| Example 3 | A | B | A | 73 | 652 |
| Example 4 | B | B | A | 53 | 651 |
| Comparative Example 1 | B | C | B | 61 | 658 |
| Comparative Example 2 | C | C | C | — | — |
| Comparative Example 3 | C | C | C | — | — |

As indicated in Table 1, the composition containing the azo compound (1A) had excellent storage stability and was capable of forming a high-quality polarizing film.

The invention claimed is:

1. An azo compound represented by the following formula (1):

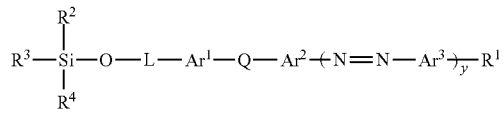

wherein in formula (1), L represents a divalent linking group or a single bond formed from at least one selected from the group consisting of a methylene group, an oxygen atom, and a carbonyl group;

y represents an integer of 1 or 2;

$R^1$ represents one group selected from the group consisting of a methylamino group, an ethylamino group, a dimethylamino group, a diethylamino group, an ethylmethylamino group, a pyrrolidyl group, an oxazolidinyl group, a piperidyl group, a morpholino group, a methoxy group, and an ethoxy group, and a hydrogen atom of each of these groups may be replaced with a polymerizable group;

$R^2$, $R^3$, and $R^4$ each independently represent an aliphatic hydrocarbon group having 1 to 10 carbon atoms, and a hydrogen atom of $R^2$, $R^3$, or $R^4$ may be replaced with a polymerizable group;

Q represents one group selected from the group consisting of —OC(=O)—, —C(=O)O—, —C=C—, —CH=CH—, —N=N—, —NHC(=O)—, and —C(=O)NH—;

$Ar^1$, $Ar^2$, and $Ar^3$ each independently represent a 1,4-phenylene group optionally having a substituent or a divalent sulfur-containing aromatic heterocyclic group optionally having a substituent; and when y is 2, two $Ar^3$ may be the same or different.

2. A composition comprising the azo compound according to claim 1, and a liquid crystalline compound containing at least one of a polymerizable liquid crystal compound and a liquid crystalline polymer compound.

3. The composition according to claim 2, wherein the liquid crystalline compound is a smectic liquid crystalline compound.

4. A film comprising the composition according to claim 2 as a forming material.

5. A laminate comprising the film according to claim 4.

6. A display device comprising the film according to claim 4.

7. A display device comprising the laminate according to claim 5.

8. The azo compound according to claim 1, wherein Q is —N=N— in the formula (1).

9. The azo compound according to claim 1, wherein at least one of $Ar^1$ and $Ar^2$ is a divalent sulfur-containing aromatic heterocyclic group in the formula (1).

* * * * *